United States Patent
Newington et al.

(10) Patent No.: US 8,202,511 B2
(45) Date of Patent: Jun. 19, 2012

(54) CONTRAST AGENTS

(75) Inventors: Ian Martin Newington, Buckinghamshire (GB); Duncan George Wynn, Buckinghamshire (GB); Veronique Morisson-Iveson, Buckinghamshire (GB); Joanna Marie Passmore, Buckinghamshire (GB)

(73) Assignee: GE Healthcare AS, Oslo (NO)

( * ) Notice: Subject to any disclaimer, the term of this patent is extended or adjusted under 35 U.S.C. 154(b) by 193 days.

(21) Appl. No.: 12/682,298

(22) PCT Filed: Oct. 10, 2008

(86) PCT No.: PCT/EP2008/063589
§ 371 (c)(1),
(2), (4) Date: Apr. 9, 2010

(87) PCT Pub. No.: WO2009/047319
PCT Pub. Date: Apr. 16, 2009

(65) Prior Publication Data
US 2010/0221189 A1    Sep. 2, 2010

(30) Foreign Application Priority Data

Oct. 12, 2007 (NO) .................................... 20075250
Nov. 30, 2007 (NO) .................................... 20076192

(51) Int. Cl.
*A61K 49/04* (2006.01)

(52) U.S. Cl. ............. 424/9.452; 424/9.4; 424/9.45; 424/9.451; 424/9.453; 424/9.454

(58) Field of Classification Search ............. 424/9.452, 424/9.453, 9.451, 9.45, 9.4, 9.454
See application file for complete search history.

(56) References Cited

U.S. PATENT DOCUMENTS

| 4,005,188 A | 1/1977 | Tilly et al. |
| 4,062,934 A | 12/1977 | Tilly et al. |
| 5,695,742 A * | 12/1997 | Felder et al. ............ 424/9.455 |
| 2009/0098059 A1* | 4/2009 | Wynn .................... 424/9.452 |

FOREIGN PATENT DOCUMENTS

| GB | 1488904 | 11/1977 |
| WO | 9208691 | 5/1992 |
| WO | 92/16498 | 10/1992 |
| WO | 95/01966 | 1/1995 |

OTHER PUBLICATIONS

PCT/EP2008/063589 ISRWO Dated Jan. 20, 2009.

* cited by examiner

*Primary Examiner* — Michael G Hartley
*Assistant Examiner* — Leah Schlientz

(57) ABSTRACT

The present invention relates to a class of compounds and to diagnostic compositions containing such compounds where the compounds are iodine containing compounds. The invention also relates to the use of such diagnostic compositions as contrast agents in diagnostic imaging and in particular in X-ray imaging, and to contrast media containing such compounds.

12 Claims, No Drawings

CONTRAST AGENTS

This application is a filing under 35 U.S.C. 371 of International application number PCT/EP2008/063589, filed Oct. 10, 2008, which claims priority to Norwegian application number 20075250 filed Oct. 12, 2007 and Norwegian application number 20076192 filed Nov. 30, 2007, the entire disclosure of each of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing two linked iodinated phenyl groups.

The invention also relates to the use of such diagnostic compositions as contrast agents in diagnostic imaging and in particular in X-ray imaging, and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™) nonionic monomers such as iohexyl (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

In patients with acute renal failure, nephropathy induced by contrast medium remains one of the most clinically important complications of the use of iodinated contrast medium. Aspelin, P et al, The New England Journal of Medicine, Vol. 348:491-499 (2003) concluded that nephropathy induced by contrast medium may be less likely to develop in high risk patients when iodixanol is used rather than a low-osmolar, non-ionic contrast medium.

The part of the patient population considered as high risk patients is increasing. To meet the need for continuous improvement of in vivo X-ray diagnostic agents for the entire patient population, there is a continuous drive in finding X-ray contrast agents that has improved properties, also with regards to contrast induced nephrotoxicity (CIN).

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast media containing a chemical compound as the active pharmaceutical ingredient(s) having two triiodinated phenyl groups linked by a linking group are usually referred to as dimeric contrast agents or dimers. During the years a wide variety of iodinated dimers have been proposed. Relevant patent publications comprises EP 1186305, EP 686046, EP108638, EP 0049745, EP 0023992, WO 2003080554, WO2000026179, WO 1997000240, WO 9208691, U.S. Pat. No. 3,804,892, U.S. Pat. No. 4,239,747, U.S. Pat. No. 3,763,226, U.S. Pat. No. 3,763,227 and U.S. Pat. No. 3,678,152. At this time, one contrast medium having an iodinated non-ionic dimer as the active pharmaceutical ingredient is one the market, the product Visipaque™ containing the compound iodixanol. The compound Hexabrix™, containing the ionic dimeric compound ioxaglic acid is also on the market.

U.S. Pat. No. 4,062,934 of Laboratoires Andre Guerbet and U.S. Pat. No. 4,139,605 of Bracco Industria Chimica S.p.a proposes symmetrical or asymmetrical iodinated dimeric compounds e.g. linked with a bis-carboxamide-ethane linking group and exemplifies a couple of these compounds. However, none of the compounds prepared in U.S. Pat. No. 4,062,934 and U.S. Pat. No. 4,139,605 are developed and brought to the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose and any additional adverse effect known or discovered for such iodinated compounds.

SUMMARY OF THE INVENTION

The present invention provides compounds useful as contrast media having desired properties with regards to at least one of the criteria mentioned above, and in particular to renal toxicity, osmolality, viscosity and solubility. The contrast media comprises iodine containing contrast enhancing compounds where iodine containing compounds are chemical compounds containing two linked iodinated phenyl groups. The iodine containing contrast enhancing compounds can be synthesized from commercially available and relatively inexpensive starting materials.

DETAILED DESCRIPTION OF THE INVENTION

The new compounds of the invention, their use as X-ray contrast agents, their formulation and production are specified in the attached claims and in the specification hereinafter.

The contrast enhancing compounds are synthetic chemical compounds of formula (I)

Formula (I)

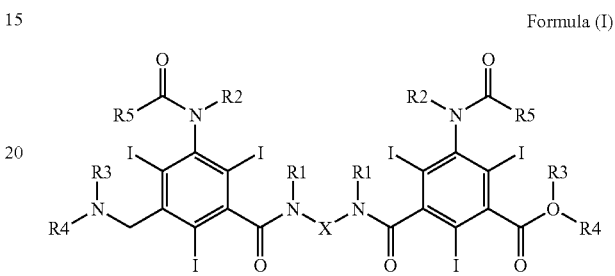

and salts or optical active isomers thereof,
wherein
each $R^1$ independently are the same or different and denotes a hydrogen atom or a $C_1$ to $C_4$ straight or branched alkyl group which is optionally substituted by 1 to 4 —OH groups;
each $R^2$ independently are the same or different and denotes a hydrogen atom or a $C_1$ to $C_4$ straight or branched alkyl group;
each $R^3$ independently are the same or different and denotes a hydrogen atom or a $C_1$ to $C_4$ straight or branched alkyl group which is optionally substituted by 1 to 4 —OH groups;
each $R^4$ independently are the same or different and denote $C_1$ to $C_6$ straight or branched alkyl moieties substituted by up to 6 —OH groups;
each $R^5$ independently are the same or different and denote $C_1$ to $C_6$ straight or branched alkyl moieties substituted by up to 6 —OH groups; and
X denotes a straight chain alkylene moiety with 3 to 10 carbon atoms, a 1,4-cyclohexylene group, or X together with the adjacent —$NR^1$ groups forms a 1,4-piperazine group or a 4-aminopiperidine group.

In formula (I) above, each of the $R^1$ substituents preferably denote a hydrogen atom, a methyl group and/or a 2-hydroxyethyl group.

The $R^2$ groups each preferably denote a hydrogen atom and/or a methyl group. Further, each of the $R^2$ groups are preferably the same, and most preferred, each of the $R^2$ groups denotes a hydrogen atom.

The $R^3$ groups each preferably denote a hydrogen atom, a methyl group and/or a 2-hydroxyethyl group. Further, each of the $R^3$ groups are preferably the same, and most preferred, each of the $R^3$ groups denote a hydrogen atom or a methyl group.

The substituents $R^4$ each preferably denote a mono-, di- and tri-hydroxylated $C_1$ to $C_6$ straight chain alkyl group. It is further preferred that the alkyl groups carry a hydroxyl group in the ω position and that the alkyl chain is not substituted in the α position. More preferred $R^4$ denotes mono- or dihydroxylated propyl moieties and/or hydroxyethyl moieties. Still more preferred each $R^4$ group is also the same, and most preferably denotes a 2,3 di-hydroxypropyl moieties.

The substituent $R^5$ preferably denotes a di- and tri-hydroxylated $C_1$ to $C_4$ straight chain alkyl group. It is further preferred that the alkyl groups carry a hydroxyl group in the ω position. More preferred $R^5$ are di- or tri-hydroxylated propyl moieties, mono- or di-hydroxyethyl moieties or hydroxymethyl.

The linker group X preferably denotes a straight chain propylene, butylene, pentylene or hexylene group. Also preferred are linker cyclic linker groups such as a 1,4-cyclohexylene group or that X together with the adjacent —$NR^1$ groups forms a 1,4-piperazine group or a 4-aminopiperidine group.

Thus, preferred structures according to the invention include the compounds of formula (IIa) to (IIz14):

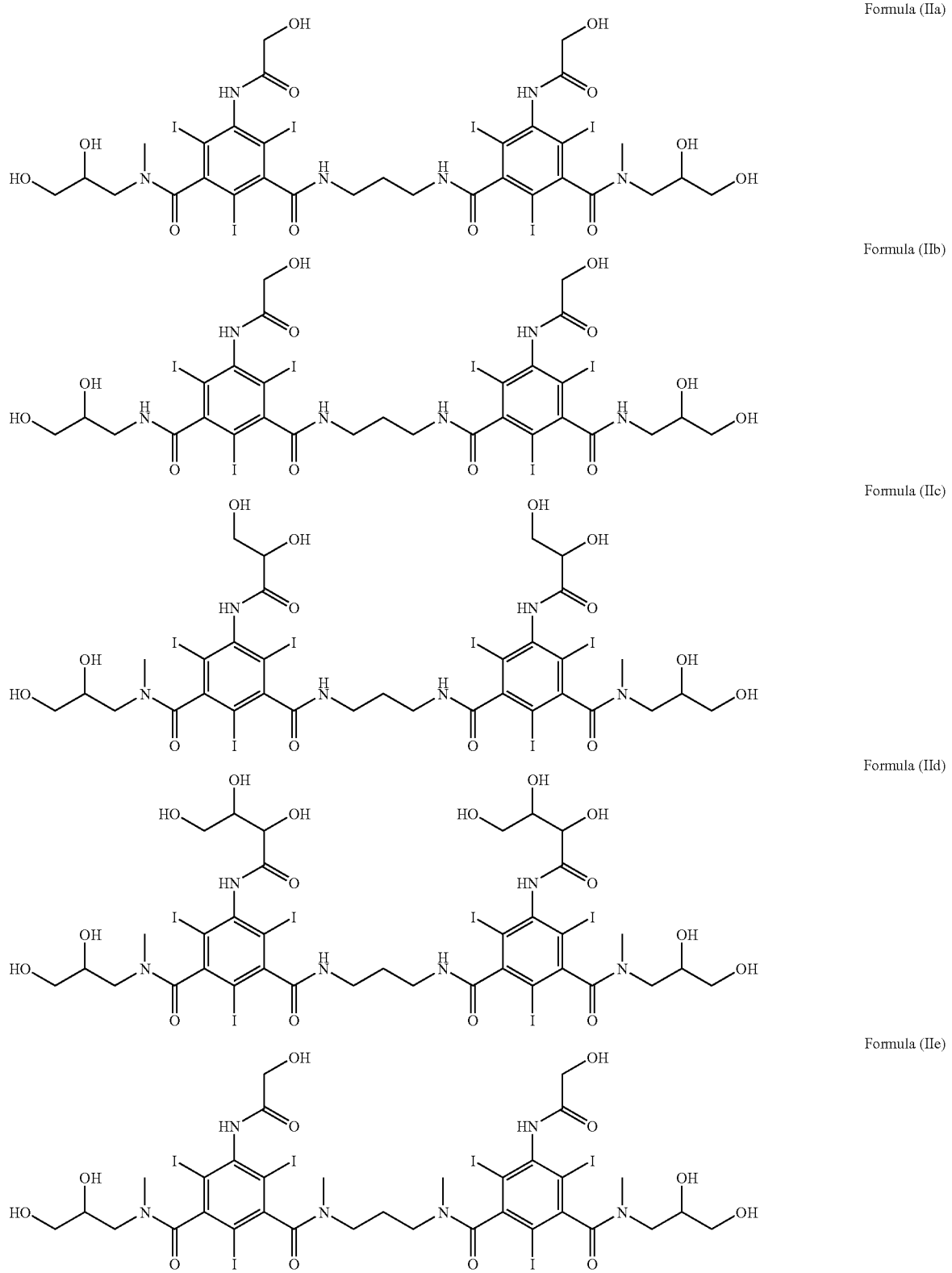

Formula (IIa)

Formula (IIb)

Formula (IIc)

Formula (IId)

Formula (IIe)

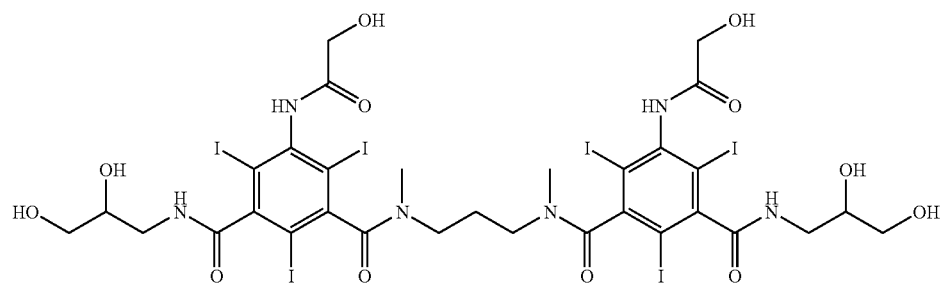
Formula (IIf)
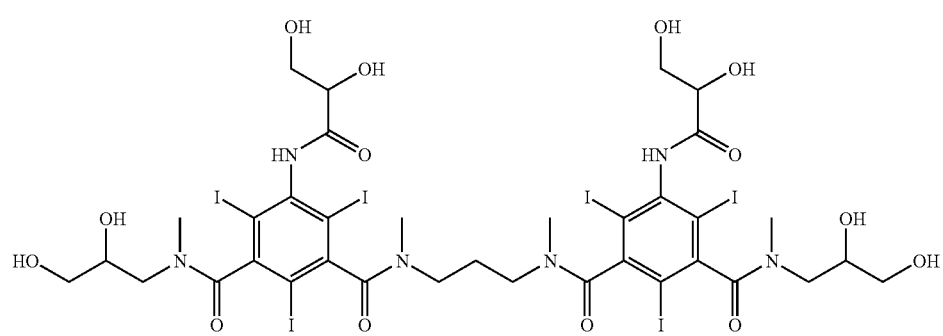
Formula (IIg)
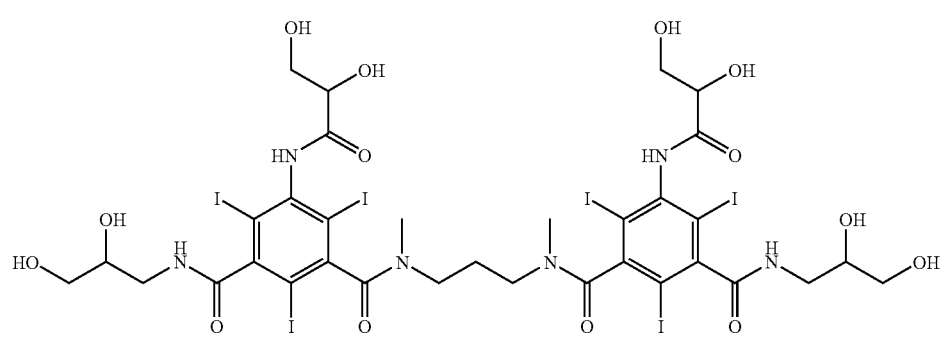
Formula (IIh)
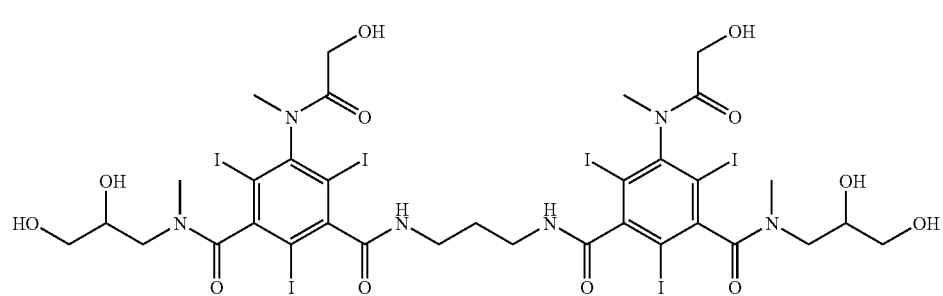
Formula (IIi)
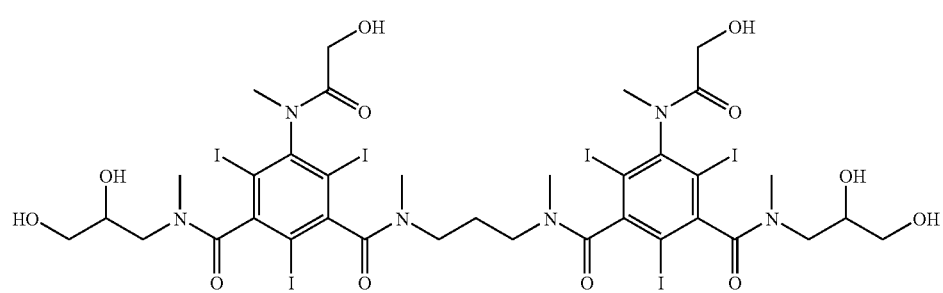
Formula (IIj)

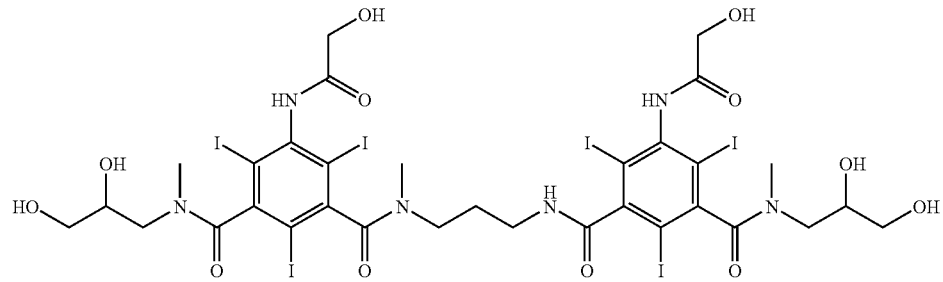
Formula (IIk)
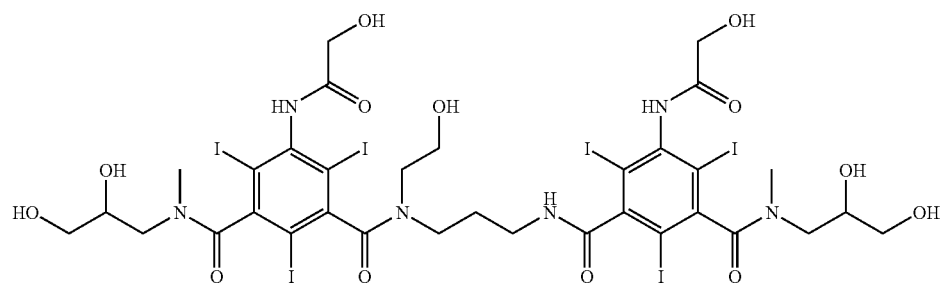
Formula (IIl)
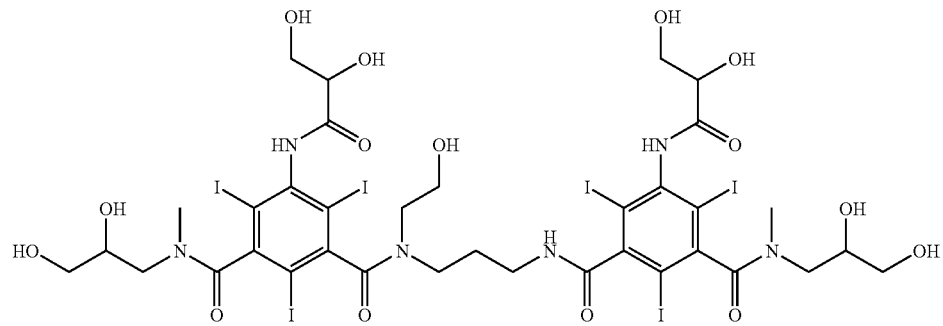
Formula (IIm)
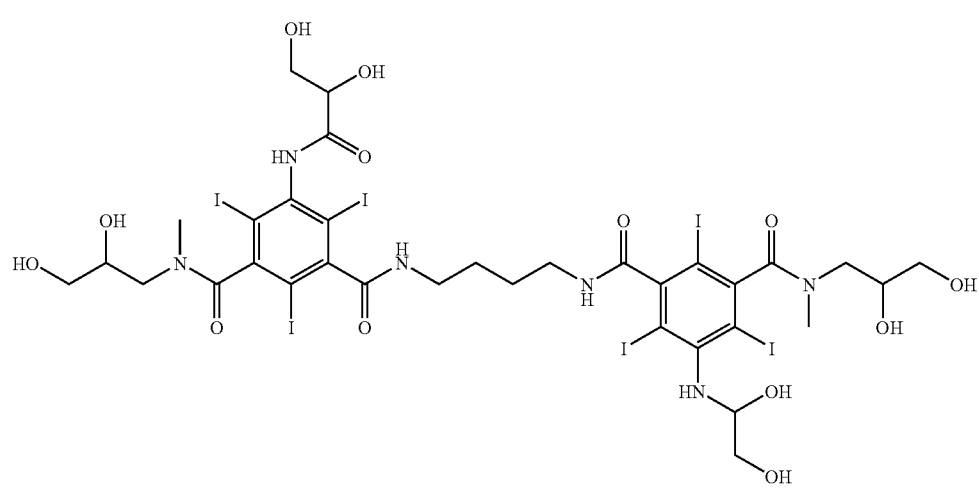
Formula (IIn)

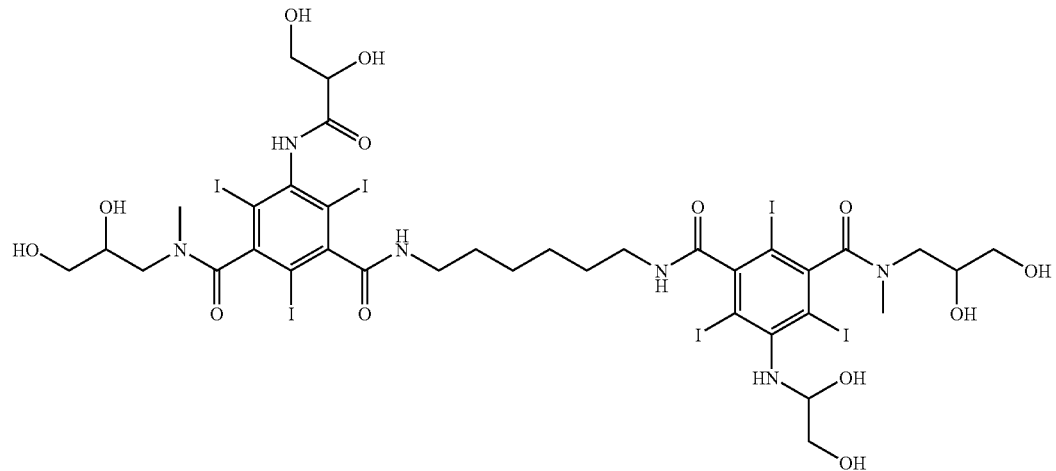
Formula (IIo)
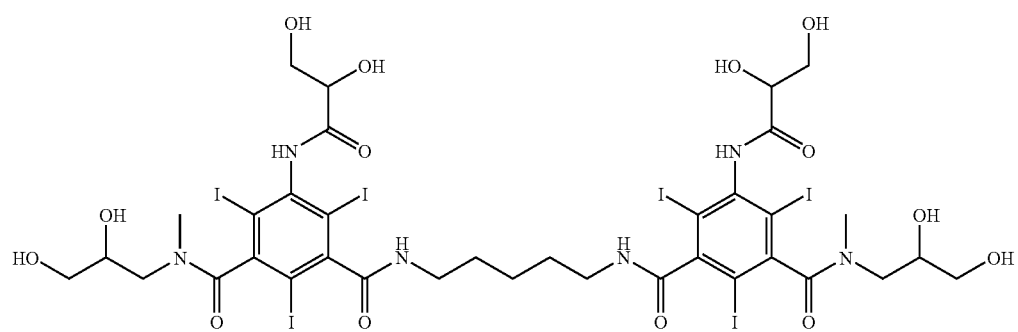
Formula (IIp)
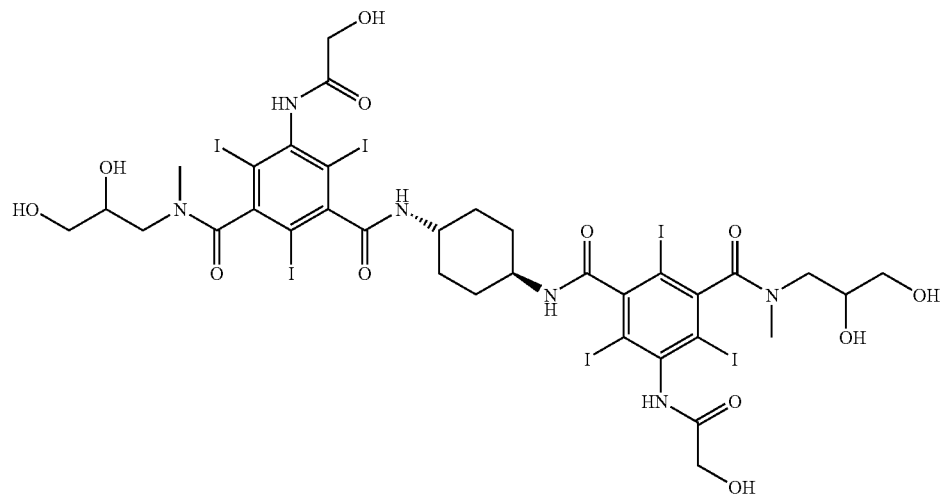
Formula (IIq)

-continued
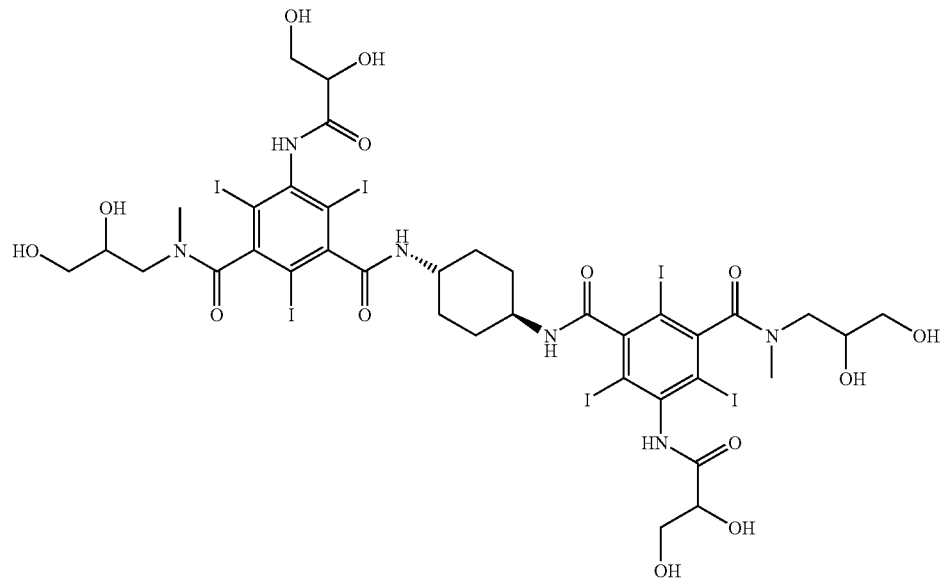
Formula (IIr)
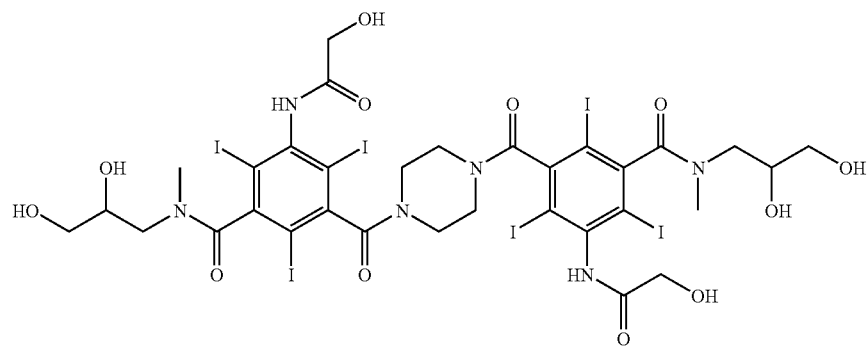
Formula (IIs)
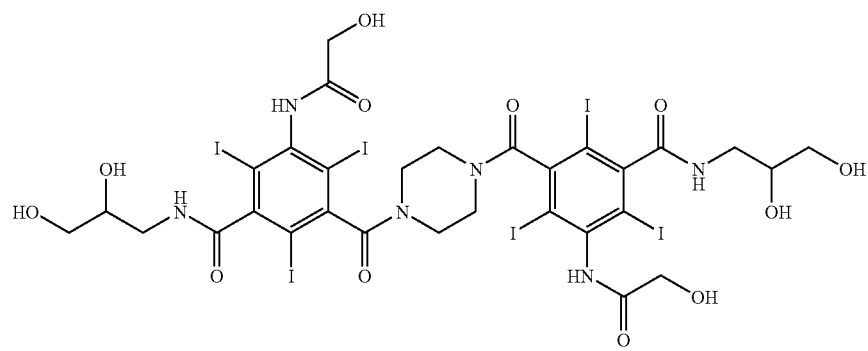
Formula (IIt)

Formula (IIu)
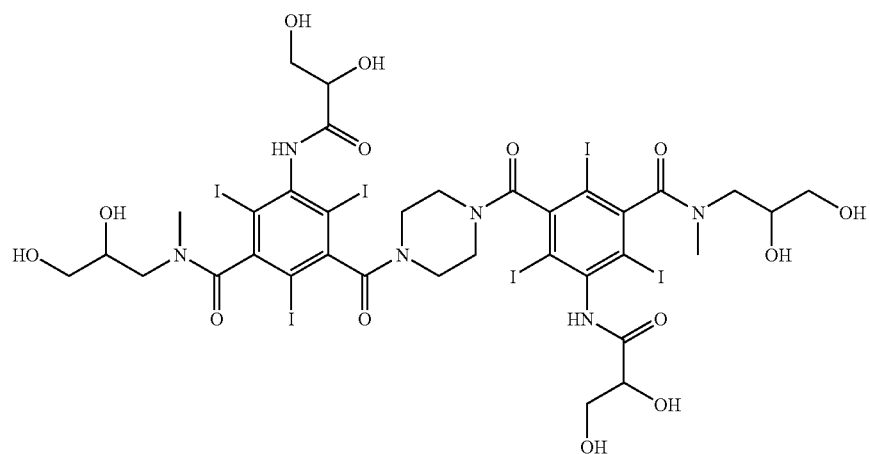
Formula (IIv)
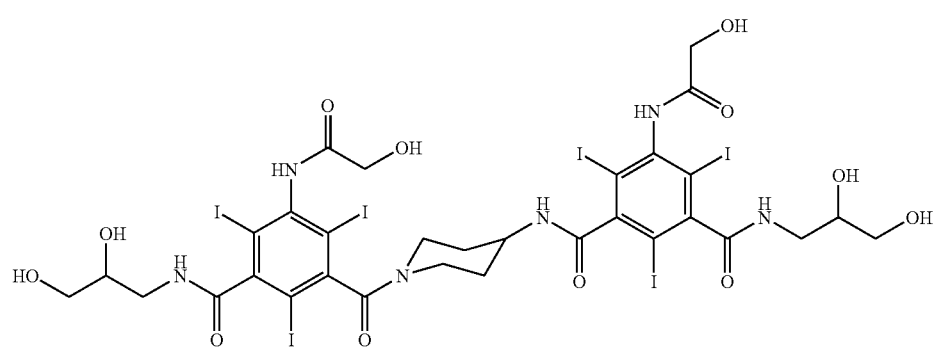
Formula (IIw)
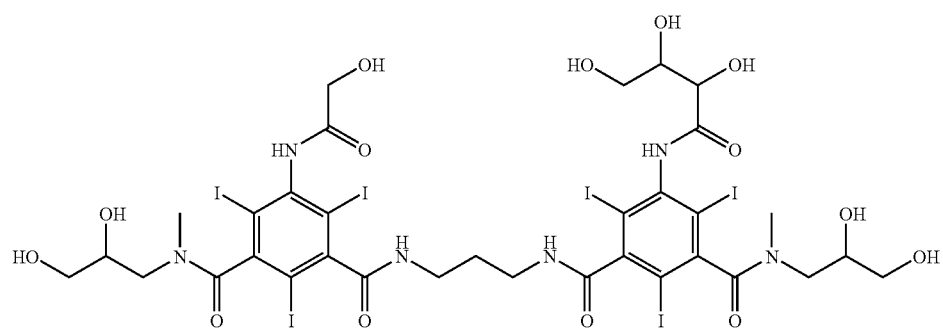
Formula (IIx)
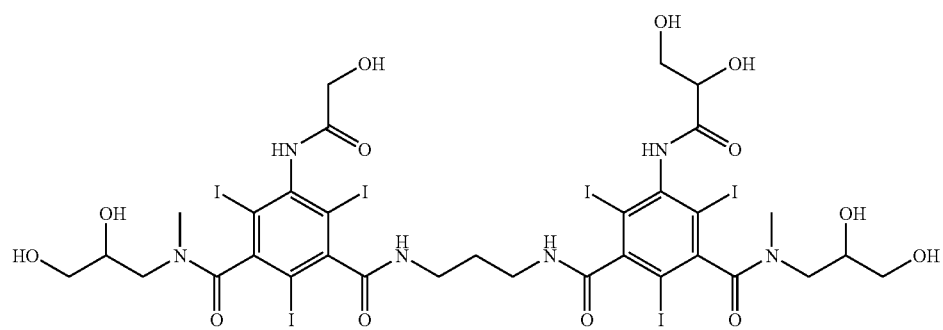

-continued
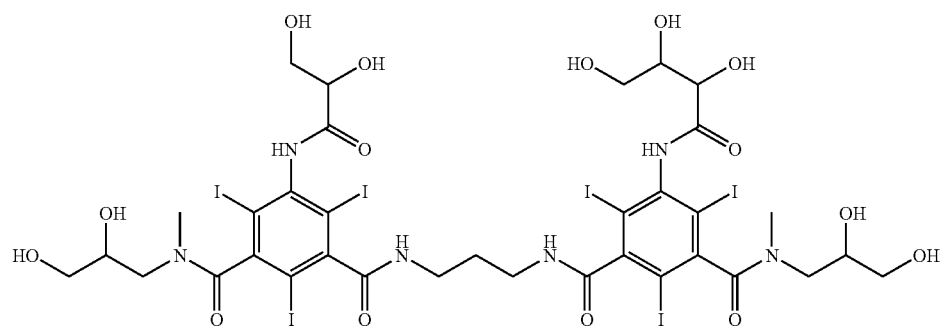
Formula (IIy)
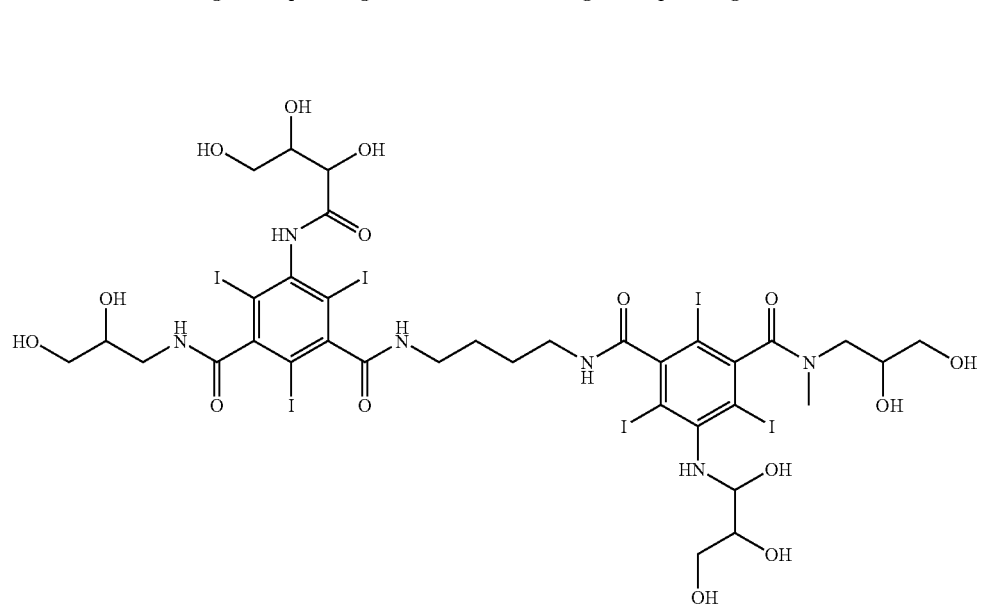
Formula (IIz)
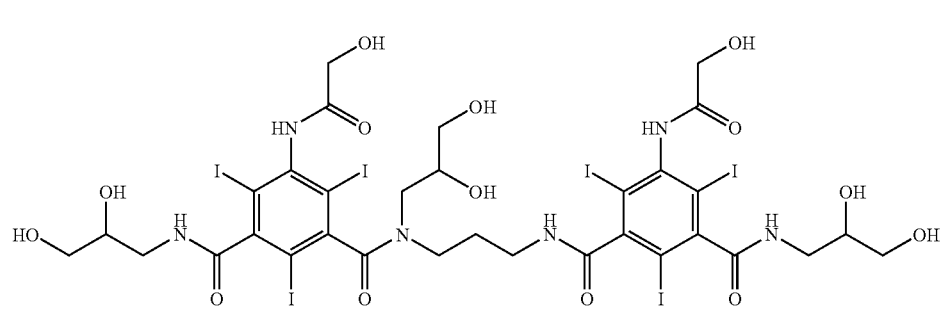
Formula (IIz1)
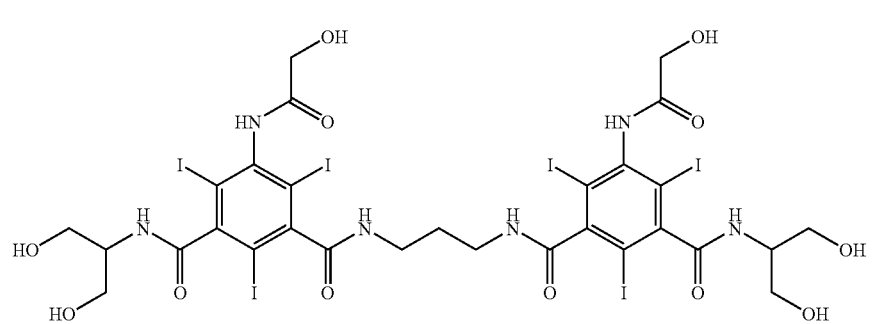
Formula (IIz2)

-continued
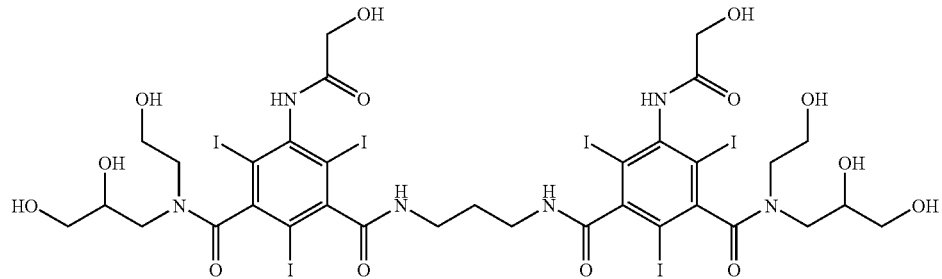
Formula (IIz3)
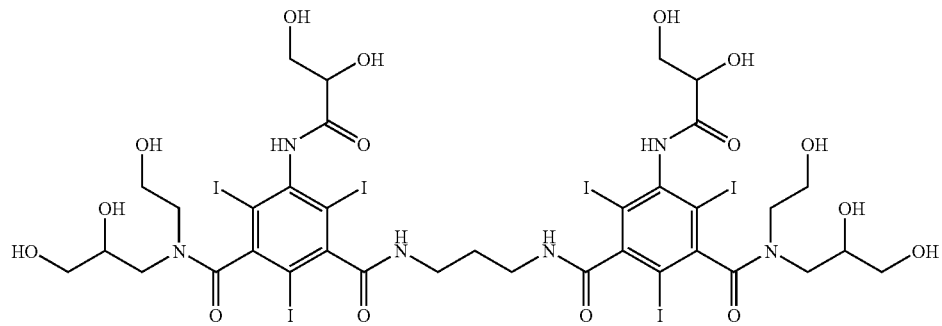
Formula (IIz4)
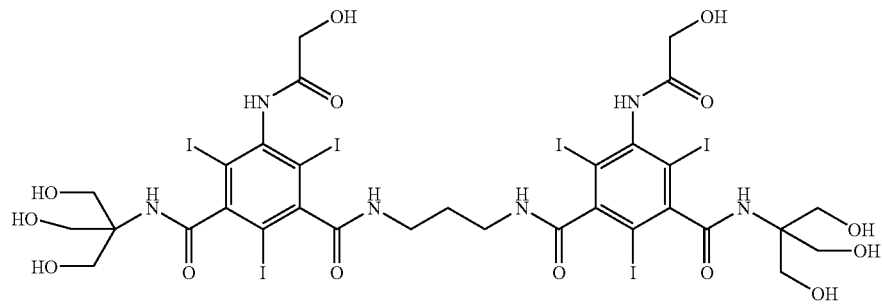
Formula (IIz5)
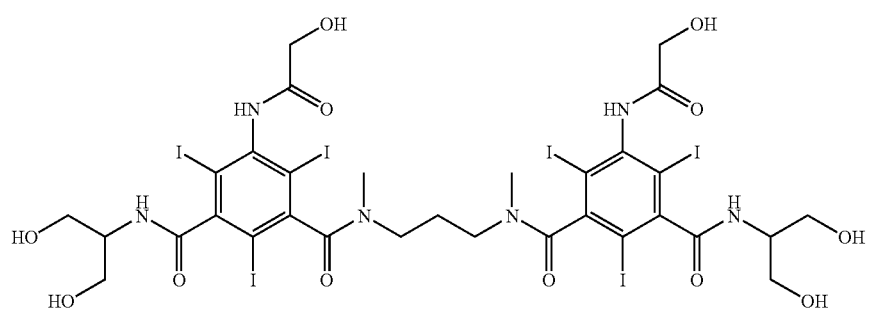
Formula (IIz6)
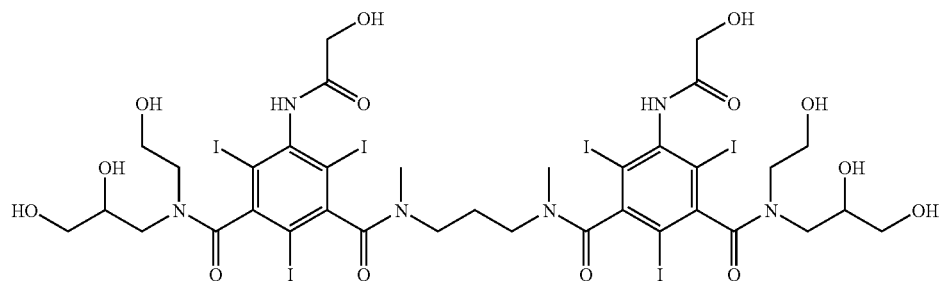
Formula (IIz7)

-continued
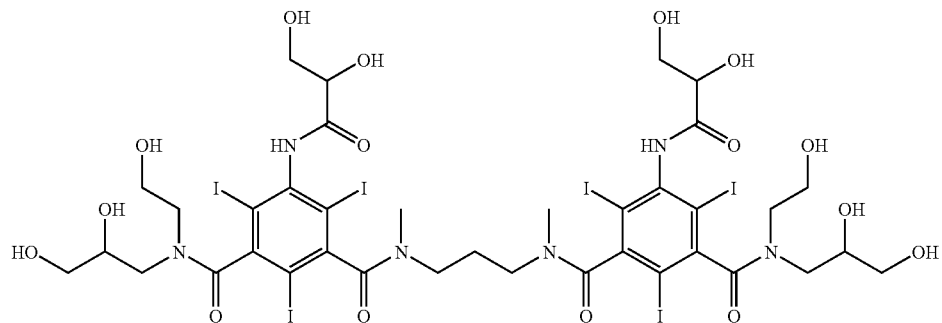
Formula (IIz8)
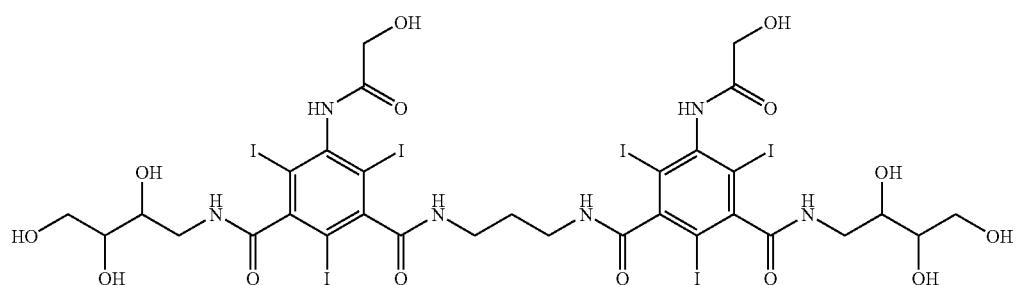
Formula (IIz9)
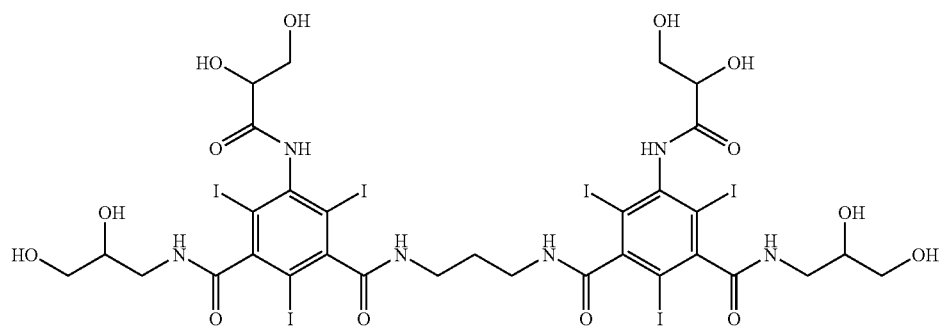
Formula (IIz10)
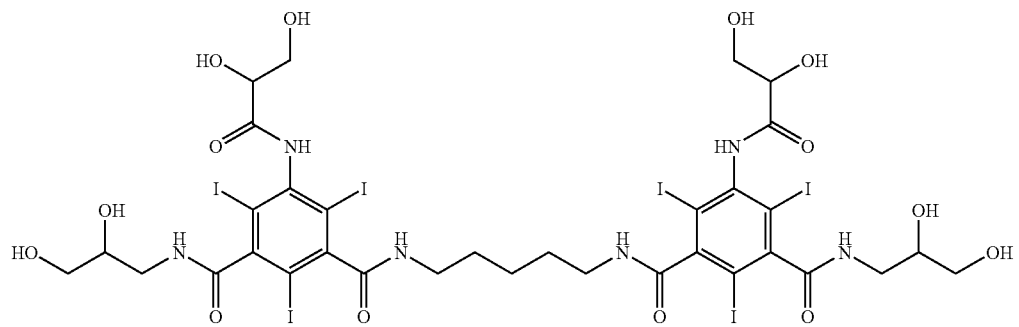
Formula (IIz11)
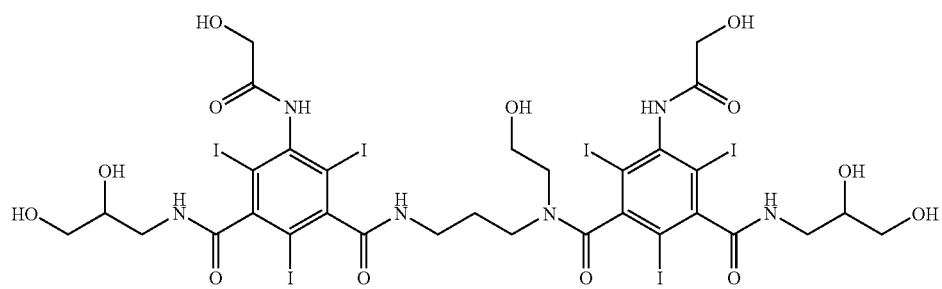
Formula (IIz12)

-continued

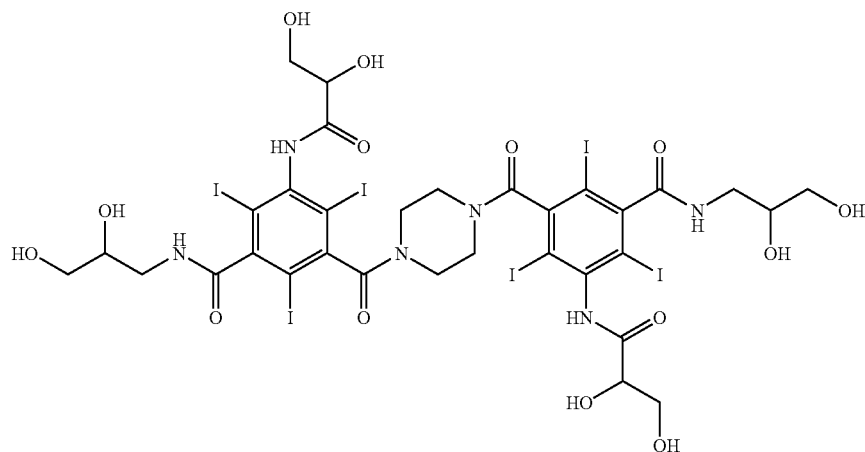

Formula (IIz13)

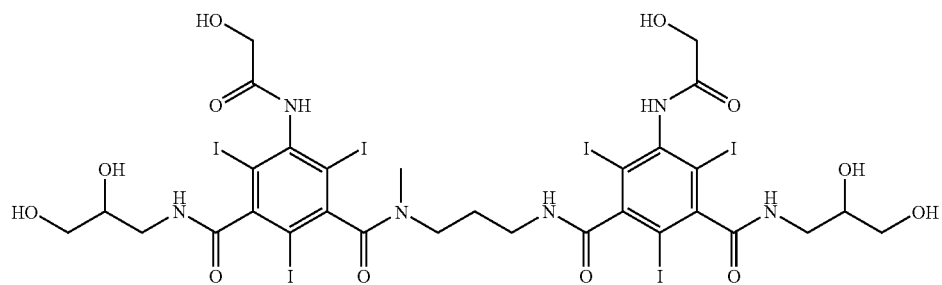

Formula (IIz14)

At an iodine concentration of 320 mg/ml, which is a common concentration for commercially available iodinated contrast media, the concentration of the compound of formula (I) will be approximately 0.42 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers and may exist in several isomeric forms due to chiral carbon atoms. In addition, the compounds exhibit exo/endo isomerism due to the restricted rotation of the amide bond caused by the proximity of the bulk iodine atom. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$, and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

The contrast media containing compounds of formula (I) can be administered by injection or infusion, e.g. by intervascular administration. Alternatively, contrast media containing compounds of formula (I) may also be administered orally. For oral administration the contrast medium may be in the form of a capsule, tablet or as liquid solution.

In a further embodiment the invention provides diagnostic agents comprising a compound of formula (I) and diagnostic compositions comprising a compound of formula (I) together with pharmaceutically acceptable carriers or excipients. The diagnostic agents and composition are preferably for use in X-ray diagnosis.

Hence, the invention further embraces use of a diagnostic agent and a diagnostic composition containing a compound of formula (I) in X-ray contrast examinations and use of a compound of formula (I) for the manufacture of a diagnostic composition for use as an X-ray contrast agent.

A method of diagnosis comprising administration of compounds of formula (I) to the human or animal body, examining the body with a diagnostic device and compiling data from the examination is also provided. In the method of diagnosis the body may also be preadministrated with compounds of formula (I).

Furthermore, a method of imaging, specifically X-ray imaging is provided, which comprises administration of compounds of formula (I) to the human or animal body, examining the body with a diagnostic device and compiling data from the examination and optionally analysing the data. In the method of imaging the body may also be preadministrated with compounds of formula (I).

Preparation

The compounds of the general formula (I) can be synthesized by multistep procedures from starting materials that are either known from the state of art or that are commercially available or can readily be produced from commercially available materials.

Compounds of formula (I) can be synthesized according to this general procedure:

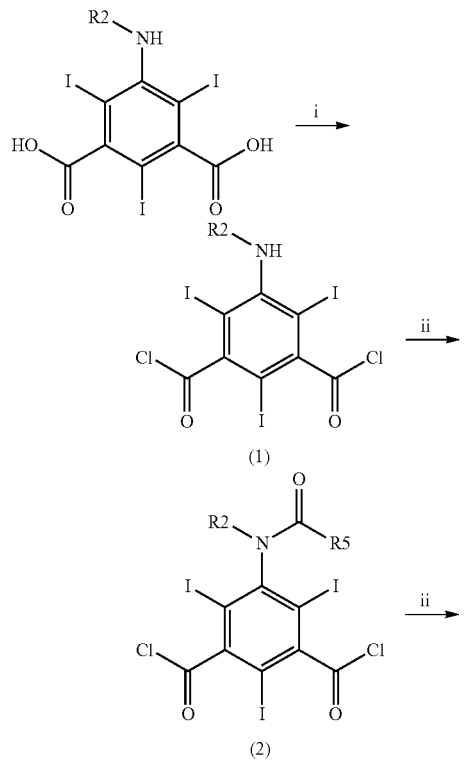

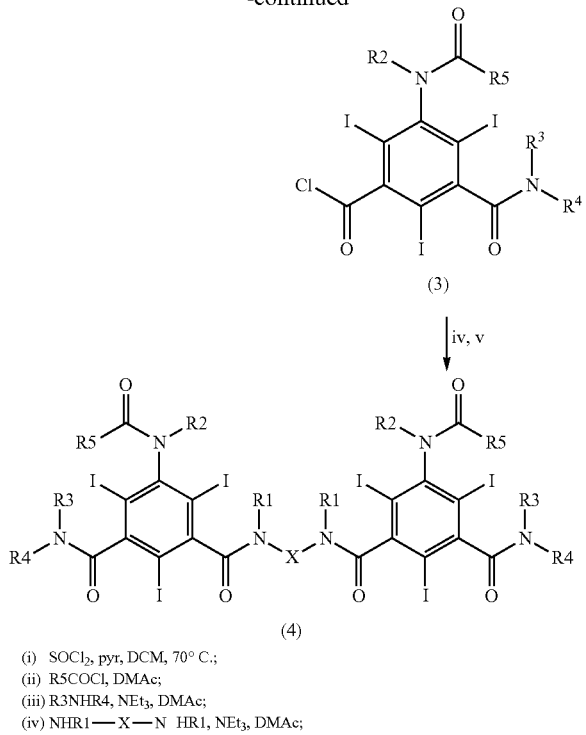

(i) SOCl$_2$, pyr, DCM, 70° C.;
(ii) R5COCl, DMAc;
(iii) R3NHR4, NEt$_3$, DMAc;
(iv) NHR1—X—N HR1, NEt$_3$, DMAc;
(v) NH$_3$, MeOH 5-amino-2,4,6-triiodo-isophtalic acid available from Aldrich is treated with thionyl chloride to form the corresponding 5-amino-2,4,6-triiodo-isophthaloyl dichloride (1). 5-Amino-2,4,6-triiodo-isophthaloyl dichloride is next reacted with either acetoxyacetyl chloride commercially available from Aldrich to form the desired N-acyl derivatives (2). N-acyl-amino-2,4,6-triiodo-isophthaloyl dichloride is then reacted with an appropriate amine such as 3-amino-1,2-propanediol to form the desired mono-amide derivatives (3). The dimer (4) is finally formed by reacting with an appropriate di-amine such as 1,3-propanediamine, N-methyl-1,3-propanediamine and, N,N'-dimethyl-1,3-propanediamine, 2-hydroxyethylamino propylamine, 1,4-diaminobutane, 1,5-diaminopentane, 1,6-diaminohexane, 1,5-bis(methylamino)-3-oxapentane, 1,2-bis(2-aminoethoxy)ethane, piperazine, 4-aminopiperidine, 1,4-cyclohexanediamine all available from Aldrich or a N-substituted derivative thereof such as 1-amino-3-(2-hydroxy-ethylamino-propane-1ol (Preparation A) with the desired mono-amide (3), follow by hydrolysis of the protecting groups.

Preparation of Intermediates

Preparation A

The commercially available Tert-butyl-N-(2-hydroxypropyl)carbamate (10 g, 57.0 mmol)) and trietylamine (12 ml, 85.6 mmol) were dissolved in dichloromethane (60 mL) and cooled to 0° C. Methanesulfonyl chloride (4.9 ml, 62.7 mmol) was added dropwise to the ice-cold solution and the reaction was allowed to warm up to room temperature with stirring overnight. The reaction was then quenched with NaOH (1M, 5 ml). The organics were washed with water (2×100 ml) and then brine, collected, dried over MgSO$_4$, filtered and evaporated under reduced pressure to give methanesulfonic acid 3-tert-butoxycarbonylamino-propyl ester (13.5 g). The crude methanesulfonic acid 3-tert-butoxycarbonylamino-propyl ester (13.5 g, 53 mmol) and 2,2-dimethyl-1,3-dioxolane-4-methanamine (12 g, 91.6 mmol) were stirred overnight at room temperature. The mixture was dissolved in ethyl acetate (100 ml) and washed with water (3×100 ml) and brine. The organics were collected, dried over MgSO$_4$, filtered and evaporated under reduced pressure to give an oil. This was purified by silica column chromatography eluting with ethyl acetate: methanol to give the desired product {2-[(2,2-Dimethyl-[1,3]dioxolan-4-ylmethyl)-amino]-propyl}-carbamic acid tert-butyl ester (4.74 g, 17.3 mmol). Mass Spec (ESI) m/z: [M+H]$^+$=289.12. $^1$H NMR (CDCl$_3$; 300 MHz) δ=5.15 (s, br, 1H), 4.19 (quin, 1H), 4.02 (t, 1H), 3.66 (t, 1H), 3.18 (q, 2H), 2.70 (m, 4H), 1.63 (quin, 2H), 1.42 (s, 9H), 1.40 (s, 3H), 1.40 (s, 3H). $^{13}$C NMR (CDCl$_3$; 300 MHz) δ=156.00, 109.05, 78.85, 75.23, 67.47, 52.30, 47.91, 39.20, 29.69, 28.35, 26.81, 25.37.

{2-[(2,2-Dimethyl-[1,3]dioxolan-4-ylmethyl)-amino]-propyl}-carbamic acid tert-butyl ester (1.5 g, 5.2 mmol) was dissolved in HCl (2N, 10 ml) and refluxed at 100° C. for 24 hours. The HCl was removed under reduced pressure to give a slurry and the desired compound was isolated by trituration with methanol and filtration to give 3-(3-Amino-propylamino)-propane-1,2-diolas the di-HCl salt (901 mg, 4.39 mmol).

Following this procedure various N-substituted 1,3 propylene-diamines can be prepared, including but not limited to:

3-(3-Amino-propylamino)-propane-1,2-diol

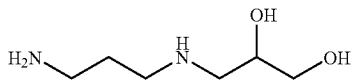

The structure was confirmed by Mass Spec (ESI) m/z: Calculated for C$_6$H$_{16}$N$_2$O$_2$ [M+H]$^+$149.207 Found 149.16. $^1$H NMR (CDCl$_3$; 300 MHz) δ=9.17 (s, br, 1H), 8.90 (s, br, 1H), 8.23 (s, br, 1H), 5.48 (s, br, 1H), 4.95 (s, br, 1H), 3.85 (m, 1H), 3.29-3.43 (m, 3H), 3.01 (m, 3H), 2.87 (m, 2H), 2.79 (m, 1H), 2.00, (quin, 2H). $^{13}$C NMR (CDCl$_3$; 300 MHz) δ=66.07, 62.25, 49.00, 43.21, 34.98, 22.37

Preparation B

To a solution of [3-(2-Hydroxy-ethylamino)-propyl]-carbamic acid tert-butyl ester (900 mg, 4.1 mmol) in THF (20 mL) was added a 1M solution of BH$_3$ in THF. The mixture was refluxed for 24 hours under nitrogen. The reaction was allowed to cool down and water (5 mL) was carefully added with vigorous stirring. The reaction mixture was concentrated to low volume and treated with a 6M aqueous solution of HCl (60 mL). The mixture was refluxed for 24 h. The mixture was concentrated to dryness then co-evaporated several time with methanol to give the desired 2-(3-methylamino-propylamino)-ethanol (399 mg, 2.46 mmol)

Following this procedure various N-methyl-N'-substituted 1,3 propylene-diamines can be prepared, including but not limited to:

2-(3-Methylamino-propylamino)-ethanol

The structure was confirmed by Mass Spec (ESI) m/z: Calculated for C$_6$H$_{16}$N$_2$O [M+H]$^+$133.207 Found 133.08, $^1$H NMR (CDCl$_3$; 300 MHz) δ=3.63 (t, 2H, J=5.19 Hz); 2.78-2.70 (m, 6H); 1.70-1.64 (m, 2H); 2.42 (s, 3H), $^{13}$C NMR (CDCl$_3$; 75 MHz) δ=60.20; 51.37; 50.07; 47.59; 36.08; 29.50.

Preparation C

5-Amino-2,4,6-triiodo-isophthaloyl dichloride was dissolved in dimethyl acetamide (DAMc) and a solution of acetoxyacetylchloride (2 eq) in DMAc was slowly added with efficient stirring. The reaction mixture was stirred overnight and the following day, the mixture was slowly poured into stirred ice water. The precipitate was filtered off and dried to give the desired material.

Following this procedure various compounds of formula (2) above can be prepared, including but not limited to:

Acetic acid (3,5-bis-chlorocarbonyl-2,4,6-triiodo-phenylcarbamoyl)-methyl ester

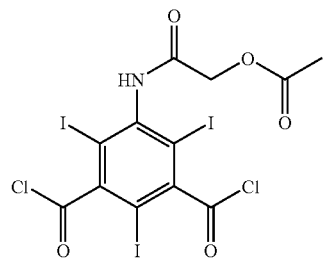

The structure was confirmed by $^1$H NMR (CDCl$_3$, 300 MHz): 10.43 (br s, 1H); 4.71 (s, 2H); 2.11 (s, 3H)

Acetic acid 2-acetoxy-1-(3,5-bis-chlorocarbonyl-2,4,6-triiodo-phenylcarbamoyl)-ethyl ester

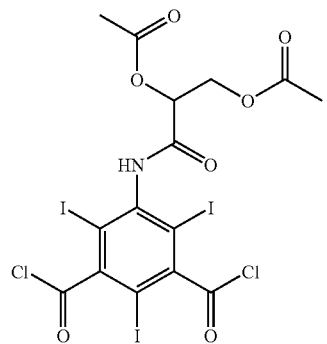

The structure was confirmed by $^1$H NMR (CDCl$_3$, 300 MHz): 10.45 (br s, 1H); 4.49-4.30 (m, 3H); 2.13 (s, 6H).

Acetic acid 2,3-diacetoxy-1-(3,5-bis-chlorocarbonyl-2,4,6-triiodo-phenylcarbamoyl)-propyl ester

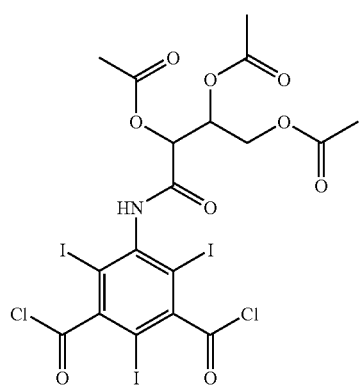

The structure was confirmed by $^1$H NMR (CDCl$_3$, 300 MHz): 8.08 (br s, 1H); 5.75-5.50 (m, 2H); 4.49-4.10 (m, 2H); 2.29 (s, 3H); 2.11 (s, 3H); 2.09 (s, 3H).

Preparation D

The bis-acid chloride from the previous step was dissolved in DMAC in a dry flask under a nitrogen atmosphere. Triethylamine (2 eq) was added to the solution immediately followed by the addition of 3-Methylamino-propane-1,2-diol (2 eq). After stirring overnight, the reaction mixture was concentrated to dryness, and the residue purified by chromatography using silica gel to give the desired product. Following this procedure various compounds of formula (3) above can be prepared, including but not limited to:

Acetic acid {3-chlorocarbonyl-5-[(2,3-dihydroxy-propyl)-methyl-carbamoyl]-2,4,6-triiodo-phenylcarbamoyl}-methyl ester

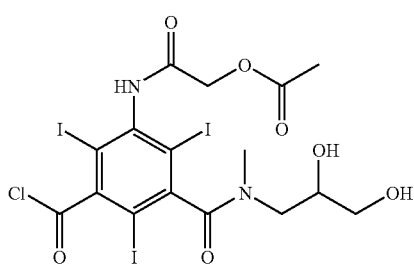

The structure was confirmed by $^1$H NMR (DMSO-D6, 300 MHz): 10.4 (br s, 1H); 4.70 (s, 2H); 3.89-3.83 (m, 1H); 3.75-3.67 (m, 1H); 3.51-3.42 (m, 2H); 3.25-3.15 (m, 1H); 2.85 (s, 3H); 2.15 (s, 3H)

Acetic acid 2-acetoxy-1-{3-chlorocarbonyl-5-[(2,3-dihydroxy-propyl)-methyl-carbamoyl]-2,4,6-triiodo-phenylcarbamoyl}-ethyl ester

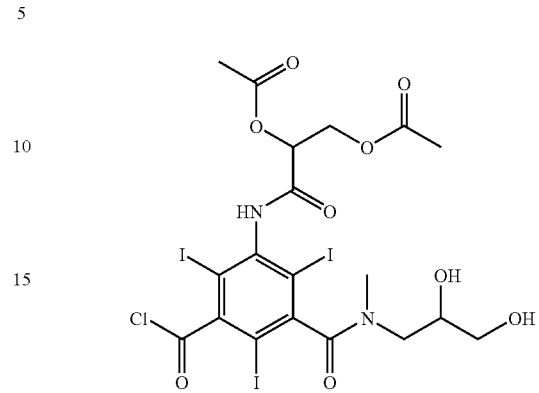

The structure was confirmed by $^1$H NMR (DMSO-D6, 300 MHz): 10.4 (br s, 1H); 4.70-4.65 (m, 3H); 3.89-3.83 (m, 1H); 3.75-3.67 (m, 1H); 3.51-3.42 (m, 2H); 3.25-3.15 (m, 1H); 2.85 (s, 3H); 2.15 (s, 6H).

Acetic acid 2,3-diacetoxy-1-{3-chlorocarbonyl-5-[(2,3-dihydroxy-propyl)-methyl-carbamoyl]-2,4,6-triiodo-phenylcarbamoyl}-propyl ester

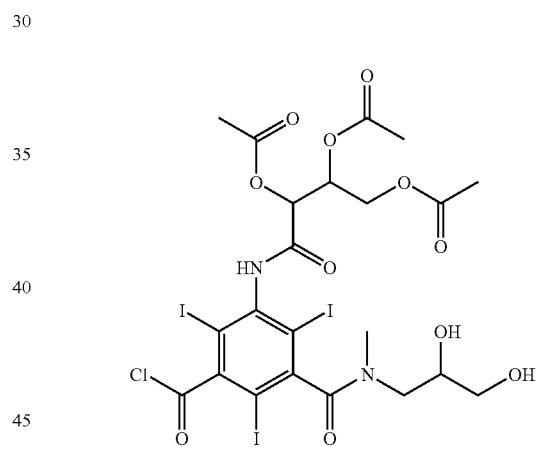

The structure was confirmed by $^1$H NMR (DMSO-D6, 300 MHz): 10.4 (br s, 1H); 5.63-5.60 (m, 2H); 4.40-4.05 (m, 2H); 4.0-2.60 (m, 2H); 3.46 (m, 2H); 3.30-3.05 (m, 1H); 2.85 (s, 3H); 2.26 (s, 3H); 2.08 (s, 3H); 2.02 (s, 3H).

Preparation E

Acetic acid (3,5-bis-chlorocarbonyl-2,4,6-triiodo-phenylcarbamoyl)-methyl ester (20 g, 25.5 mmol) was dissolved in dry DMA (100 ml) and 2,2,-dimethyl-1,3-dioxolane-4-methanaine (6.62 ml, 51 mmol) was added. The reaction was stirred for 24 hours at room temperature under nitrogen. The reaction mixture was diluted with ethyl acetate and washed with ice-water (50 ml×3) and brine. The organics were collected, dried over MgSO$_4$, filtered and evaporated to give as brown oil. This was purified by silica column chromatography eluting with petrol: ethyl acetate to give acetic acid {3-chlorocarbonyl-5-[(2,2-dimethyl-[1,3]dioxolan-4-ylmethyl)-carbamoyl]-2,4,6-triiodo-phenylcarbamoyl}-methyl ester (13.85 g, 17.5 mmol) as a pink solid. Following this procedure various compounds of formula (3) above can be prepared, including but not limited to:

Acetic acid {3-chlorocarbonyl-5-[(2,2-dimethyl-[1,3]-dioxolan-4-ylmethyl)-carbamoyl]-2,4,6-triiodo-phenylcarbamoyl}-methyl ester

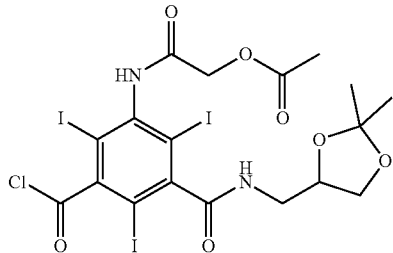

The structure was confirmed by Mass Spec (ESI) m/z: Calculated for $C_{18}H_{18}ClN_2O_7$ [M+H]$^+$791.520 Found 790.84, $^1$H NMR (DMSO; 300 MHz) δ=10.35-10.15 (m, 1H, NH), 9.03-8.87 (m, 1H, NH), 4.70 (s, 2H), 4.25 (m, 1H), 4.07 (m, 1H), 3.79 (m, 1H), 3.50-3.10 (m, 2H), 2.15 (s, 3H), 1.36 (s, 3H), 1.23 (s, 3H).

Acetic acid 2-acetoxy-1-[3-chlorocarbonyl-5-(2,3-dihydroxy-propylcarbamoyl)-2,4,6-triiodo-phenyl-carbamoyl]-ethyl ester

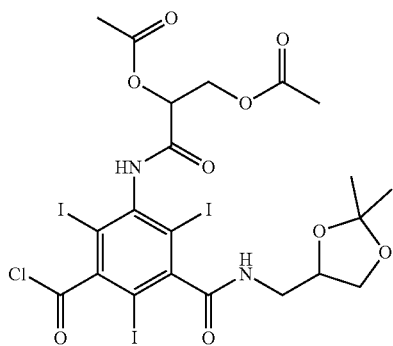

The structure was confirmed by Mass Spec (ESI) m/z: Calculated for $C_{21}H_{22}ClN_2O_9$ [M+H]$^+$863.594 Found 862.75, $^1$H NMR (CDCl$_3$; 300 MHz) δ=6.39 (s, br, 1H, NH), 5.63 (s, br, 1H, NH), 4.64 (m, 1H), 4.50 (m, 1H), 4.35 (m, 1H), 3.78-3.65 (m, 2H), 3.42 (m, 1H), 2.28 (d, 3H), 2.08 (s, 3H), (s, 3H), 1.43 (s, 3H), 1.33 (s, 3H)

Preparation F

5-Amino-2,4,6-triiodoisophthalic acid (50 g, 89.5 mol), readily available from Aldrich, was dissolved slowly in concentrated sulphuric acid (200 ml) at 50° C. The resulting purple solution was then added dropwise to formaldehyde (38% by weight, 100 ml) maintaining a temperature of between 40-50° C. The solution was stirred for 2 hours at 50° C. and then allowed to cool. The mixture was poured onto ice water (3 L) and the solid was collected by filtration and dried in a vacuum oven at 50° C. for 7 days to give 2,4,6-triiododo-5-methylamino-isophthalic acid (55.3 g). Mass Spec (ESI) m/z: [M+H]$^+$=574.36. $^{13}$C NMR (DMSO; 300 MHz) δ=169.84, 152.75, 149.44, 90.49, 80.00, 35.55.

2,4,6-Triiododo-5-methylamino-isophthalic acid (50 g, 87.3 mmol) was stirred in thionyl chloride (275 ml, 1.41 mol) and DMF (1 ml) at 70° C. for 72 hours. The thionyl chloride was removed under reduced pressure and the resulting solid was partitioned between ethyl acetate (400 ml) and ice water (200 ml). The organic layer was collected, dried over MgSO$_4$, filtered and evaporated to dryness. The product was purified by silica column chromatography eluting with petrol: ethyl acetate to give 2,4,6-Triiodo-5-methylamino-isophthaloyl dichloride (30.93 g, 50.7 mmol). Following this procedure various compounds of formula (I) above can be prepared, including but not limited to:

2,4,6-Triiodo-5-methylamino-isophthaloyl dichloride

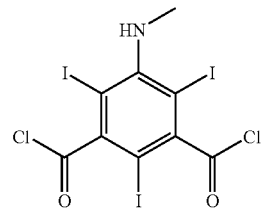

The structure was confirmed by $^{13}$C NMR (DMSO; 300 MHz) δ=169.42, 154.03, 149.85, 89.82, 75.23, 35.58.

Preparation G 2,4,6-Triiodo-5-methylamino-isophthaloyl dichloride (20 g, 32.8 mmol) was dissolved in DMA (60 ml) and acetoxy-acetyl chloride (15.32 ml, 142 mmol) was added. The reaction was stirred overnight at room temperature with nitrogen bubbling through the reaction mixture. The reaction mixture was poured slowly onto ice-water (300 ml) and a white solid was isolated by filtration. The solid was dissolved in ethyl acetate and washed with water. The ethyl acetate was collected, dried over MgSO$_4$, filtered and evaporated to give a white solid. This was purified by silica column chromatography eluting with petrol: ethyl acetate to give acetic acid [(3,5-bis-chlorocarbonyl-2,4,6-triiodo-phenyl)-methyl-carbamoyl]-methyl ester (16.25 g, 22.9 mmol).

Following this procedure various compounds of formula (I) above can be prepared, including but not limited to:

Acetic acid [(3,5-bis-chlorocarbonyl-2,4,6-triiodo-phenyl)-methyl-carbamoyl]-methyl ester

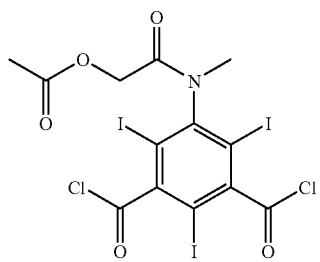

The structure was confirmed by Mass Spec (ESI) m/z: [M+H]$^+$=710.73. $^1$H NMR (CDCl$_3$; 300 MHz) δ=4.32 (s, 2H), 3.26 (s, 3H), 2.13 (s, 3H) $^{13}$C NMR (CDCl$_3$; 300 MHz) δ=170.11, 165.19, 151.89, 147.88, 95.91, 84.21, 62.39, 34.17, 20.47.

Preparation H

Acetic acid [(3,5-bis-chlorocarbonyl-2,4,6-triiodo-phenyl)-methyl-carbamoyl]-methyl ester (16.25 g, 22.9 mmol) and 3-methylamino-1,2,-propanediol (4.42 ml, 45.8 mmol) were stirred in DMA (80 ml) for 72 hours at room temperature. The mixture was diluted with ethyl acetate (150 ml) and washed with ice water/brine (50:50, 20 ml×3). The organics were collected, dried over MgSO$_4$, filtered and evaporated to dryness. The product was purified by silica column chromatography eluting with DCM: methanol to give acetic acid ({3-chlorocarbonyl-5-[(2,3-dihydroxy-propyl)-methyl-carbamoyl]-2,4,6-triiodo-phenyl}-methyl-carbamoyl)-methyl ester (5.42 g, 6.96 mmol).

Following this procedure various compounds of formula (3) above can be prepared, including but not limited to:

Acetic acid ({3-chlorocarbonyl-5-[(2,3-dihydroxy-propyl)-methyl-carbamoyl]-2,4,6-triiodo-phenyl}-methyl-carbamoyl)-methyl ester

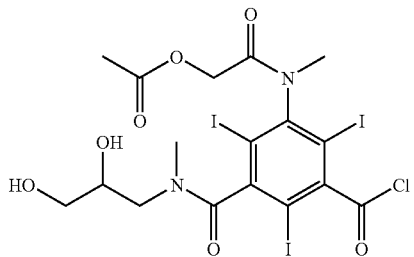

The structure was confirmed by Mass Spec (ESI) m/z: [M+H]$^+$=778.72.

Preparation I

N-(Hydroxyethyl)-Amino-2,3-propanediol

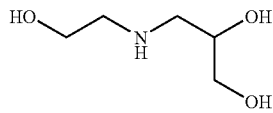

The commercially available glycidol (0.17 mol, 11 ml) was added dropwise to stirred ethanolamine (1 eq, 1.4 mol, 84.3 ml) at 0° C. Once addition was complete the reaction was allowed to warm up to room temperature, while stirring overnight. The product was then distilled (Ethanolamine first distilled at 60° C. at 1 Torr, and the desired product at 170° C. at 1 Torr). The product was obtained a clear oil that cooled to a clear viscous syrup (0.122 mol, yield=72%).

The structure was confirmed by $^{13}$C NMR (D$_2$O; 300 MHz) δ=50.21, 50.86, 60.36, 64.20, 70.63. $^1$H NMR (D$_2$O; 300 MHz) δ=2.55-2.75 (m, 4H) 3.45-3.7 (m, 4H) 3.75-3.85 (m, 1H)

Preparation J

2-[(2,2-Dimethyl-[1,3]dioxolan-4-yl-methyl)-amino]-ethanol

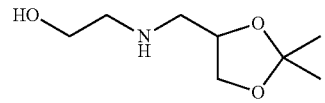

The N-(hydroxyethyl)-amino-2,3-propanediol (16.5 g, 122 mmol) was treated with a solution of HCl in dioxane (33.5 ml, 134 mmol). To this solution were added 2,2-dimethoxypropane (15.3 g, 147 mmol), DMAC (50 mL), and a catalytic amount of para-toluene sulphonic acid (0.006 mol, 1.16 g). The mixture stirred at room temperature for 24 hours. Triethylamine (1 mL) was then added, and the solvents removed by rotary evaporation. The viscous crude mixture was dissolved into triethylamine (30 mL) and ethyl acetate (500 mL) and stirred at RT for 30 min. The mixture was filtered and the collected solid washed several times with ethyl acetate. The filtrate was then evaporated on a high vacuum rotary evaporator at 40° C. to give a yellow liquid (0.122 mol, 99% yield).

The structure was confirmed by NMR. $^1$H NMR (D$_2$O; 300 MHz) δ=1.40 (s, 3H) 1.46 (s, 3H) 2.75-2.8 (m, 4H) 3.7-3.75 (m, 3H) 4.17 (dd, 1H) 4.37 (dd, 1H)

Preparation K

Acetic acid 2-acetoxy-1-{3-chlorocarbonyl-5-[(2,2-dimethyl-[1,3]dioxolan-4-ylmethyl)-(2-hydroxy-ethyl)-carbamoyl]-2,4,6-triiodo-phenylcarbamoyl}-ethyl ester

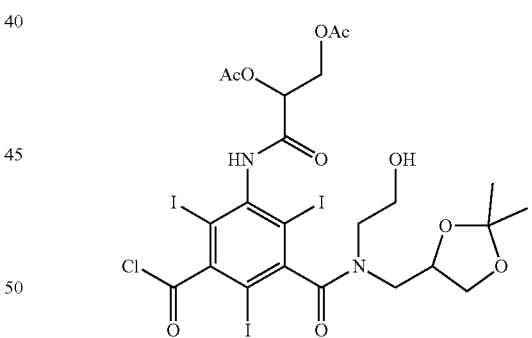

To a ice cooled solution of acetic acid 2-acetoxy-1-(3,5-bis-chlorocarbonyl-2,4,6-triiodo-phenylcarbamoyl)-ethyl ester (20 g, 0.026 mol) in anhydrous DMAC (20 ml) were added dropwise a solution of 2-[(2,2-Dimethyl-[1,3]dioxolan-4-yl-methyl)-amino]-ethanol (4.6 g, 0.026 mol) in DMAC (20 mL) followed by triethylamine (~3 g). The mixture was stirred at room temperature for 24 h and then poured over icewater (0.75 litre). A white precipitate formed. This was collected and washed with cold water. The filter cake was then dissolved in ethyl acetate and washed with brine. The organics were collected, dried over MgSO$_4$, filtered and evaporated to dryness. The product was purified by silica column chromatography eluting with Petroleum ether/ethyl acetate. Two peaks closely eluting at 80% ethyl acetate were analysed by NMR and mass spec, and show to both contain the desired material. These were combined post analysis to give the desired product (10 mmol, Yield=38%). The structure was confirmed by Mass Spec (ESI) m/z: Calculated for $C_{23}H_{26}Cl\ I_3N_2O_{10}$ [M+H]$^+$906.64. Found 906.93. $^1$H NMR (CDCl$_3$; 300 MHz) δ=1.33 (2s, 3H) 1.45 (2s, 3H) 2.02 (s, 3H) 2.26 (s, 3H) 3-3.5 (m, 4H) 3.5-3.9 (m, 3H) 3.9-4.3 (m, 2H) 4.5 (m, 1H) 4.6-4.8 (m, 2H) 5.62 (NH singlet, 1H)

Following this procedure various compounds of formula (3) above can be prepared, including but not limited to:

Acetic acid {3-chlorocarbonyl-5-[(2,2-dimethyl-[1,3]-dioxolan-4-ylmethyl)-(2-hydroxy-ethyl)-carbamoyl]-2,4,6-triiodo-phenylcarbamoyl}-methyl ester

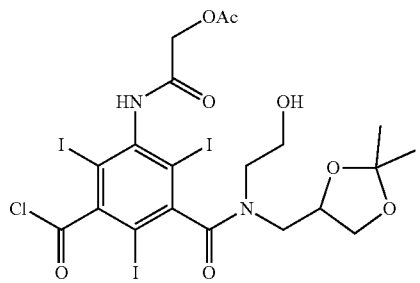

The structure was confirmed by Mass Spec (ESI) m/z: Calculated for $C_{20}H_{22}Cl\ I_3N_2O_8$[M+H]$^+$834.57. Found 834.93. $^1$H NMR (CDCl$_3$; 300 MHz) δ=1.33 (2s, 3H) 1.48 (2s, 3H) 2.26 (s, 3H) 3-3.5 (m, 3H) 3.5-4.3 (m, 5H) 4.4 (m, 1H) 4.76 (1H NH)

Preparation L (2-Hydroxy-1-hydroxymethyl-ethyl)-carbamic acid tert-butyl ester

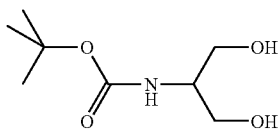

2-Amino-1,3-propanediol (5.0 g, 54.9 mmol) was dissolved in dry THF (175 ml) and triethylamine (7.7 ml) added. The solution was cooled in an ice-bath and di-tert-butylcarbonate (11.98 g, 54.9 mmol) added in portions over 15 mins. The solution was allowed to warm to ambient temperature and stirred for 90 mins. The solvent was evaporated and water (250 ml) added and the product extracted into ethyl acetate (4×125 ml). The combined organics were washed with brine, dried over magnesium sulphate, filtered and evaporated. The product was isolated by recrystallization from hot ethyl acetate-petrol (1:3) to give shiny flakes 5.18 g (49% yield). The structure was confirmed by $^1$H NMR (300 MHz, CDCl$_3$): 1.44 (s, 9H), 3.08-3.17 (m, 1H), 3.61-3.84 (m, 4H).

Preparation M

Acetic acid 3-acetoxy-2-tert-butoxycarbonylamino-propyl ester

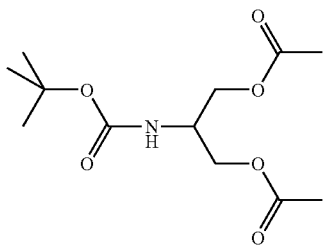

(2-Hydroxy-1-hydroxymethyl-ethyl)-carbamic acid tert-butyl ester (5.0 g, 26.1 mmol) was dissolved in pyridine (50 ml) and acetic anhydride (50 ml) was added. The solution was stirred at ambient temperature for 24 h when TLC showed no starting material remained. The solvent was evaporated and the residue dissolved in ethyl acetate (120 ml) and washed with dilute hydrochloric acid (3×50 ml), sodium bicarbonate solution (50 ml), brine, dried over magnesium sulphate, filtered and evaporated to give a colourless oil (7.2 g, 99% yield). The structure was confirmed by $^1$H NMR (300 MHz, CDCl$_3$): 1.42 (s, 9H), 2.05 (s, 6H), 4.00-4.20 (m, 4H), 4.76-4.88 (m, 1H).

Preparation N

2-Acetoxy-1-acetoxymethyl-ethyl-ammonium trifluoroacetate

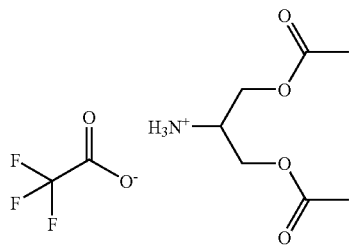

Acetic acid 3-acetoxy-2-tert-butoxycarbonylamino-propyl ester (7.2 g) was dissolved in trifluoroacetic acid (40 ml) and stirred at ambient temperature. Effervescence was rapid at the start and had stopped after 1 h when the volatiles were removed at reduced pressure to give the product as a viscous oil in quantitative yield. The structure was confirmed $^1$H NMR (300 MHz, CDCl$_3$): 2.12 (s, 9H), 3.83-3.91 (m, 1H), 4.27-4.46 (m, 4H).

Preparation O

Acetic acid 3-acetoxy-2-[3-(2-acetoxy-acetylamino)-5-chlorocarbonyl-2,4,6-triiodo-benzoylamino]-propyl ester

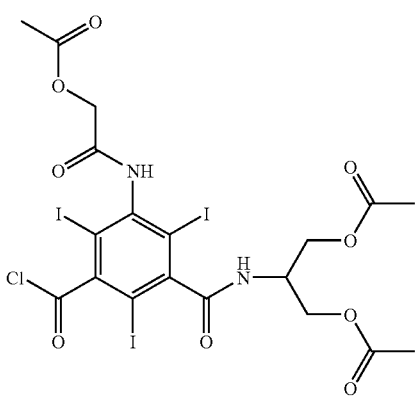

Acetic acid (3,5-bis-chlorocarbonyl-2,4,6-triiodo-phenylcarbamoyl)-methyl ester (4.82 g, 6.92 mmol) was added to a solution of 2-Acetoxy-1-acetoxymethyl-ethyl-ammonium trifluoroacetate (2.0 g, 6.92 mmol) in dimethylacetamide (30 ml) with triethylamine 2 ml, 15.8 mmol). The solution was heated at 40° C. for 18 h followed by 60° C. for 4 h. The reaction mixture was diluted with ethyl acetate (350 ml) and washed with ice-water (4×50 ml), brine (50 ml), dried over sodium sulphate, filtered and evaporated. The crude product was purified by chromatography on silica gel using ethyl acetate and petrol eluant to give the product as a white solid foam (1.11 g, 38% yield).

The structure was confirmed by Mass Spec (ESI) m/z: Calculated for $C_{19}H_{18}Cl\ I_3N_2O_9[M+H]^+$ 834.53. Found 834.84

Preparation P (5-Amino-2,2-dimethyl-[1,3]dioxan-5-yl)-methanol

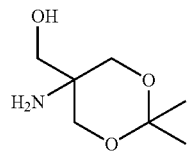

Tris hydrochloride (51 g, 324 mmol) was suspended in dry DMF (100 ml) and 2,2-dimethoxypropane (39 g, 374 mmol) was added followed by para-toluenesulfonic acid (2.6 g, 13.5 mmol). The mixture was stirred in a sealed flask for 18 h at ambient temperature when a clear solution resulted. Triethylamine (2.5 ml) was added and solvent evaporated. The viscous crude was dissolved in triethylamine (40 ml) and ethyl acetate (750 ml) added and the white precipitate of ammonium salts was filtered off after stirring for 30 mins. The filtrate was evaporated to give the product as a colourless liquid in approx. 85% yield.

The structure was confirmed by $^1$H NMR (300 MHz, CDCl$_3$): 1.38 (s, 3H), 1.41 (s, 3H), 3.48 (s, 2H), 3.53 (d, 2H) and 3.77 (d, 2H).

Preparation Q

Acetic acid [3-chlorocarbonyl-5-(5-hydroxymethyl-2,2-dimethyl-[1,3]dioxan-5-ylcarbamoyl)-2,4,6-triiodo-phenylcarbamoyl]-methyl ester

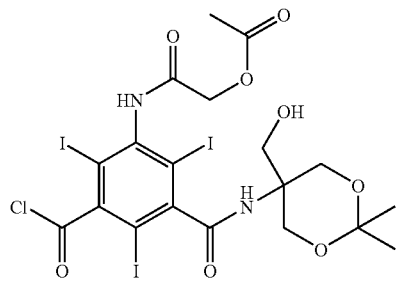

(5-Amino-2,2-dimethyl-[1,3]dioxan-5-yl)-methanol (9.5 g, 58.9 mmol) was dissolved in dimethylacetamide (100 ml) and triethylamine (2 ml) added. Acetic acid (3,5-bis-chlorocarbonyl-2,4,6-triiodo-phenylcarbamoyl)-methyl ester (21.0 g, 30.2 mmol) was added and the mixture heated under nitrogen at 60° C. for 24 h. On cooling, ethyl acetate (1.2 l) was added and the solution washed with ice-water (4×120 ml), brine, dried over sodium sulphate, filtered and evaporated to give the crude product. The pure product obtained as a white solid by chromatography on silica gel (8.32 g, 34% yield).

The structure was confirmed by Mass Spec (ESI) m/z: Calculated for $C_{19}H_{20}Cl\ I_3N_2O_8\ [M+H]^+$ 820.546. Found 818.89

Preparation R

4-Dibenzylamino-butane-1,2,3-triol

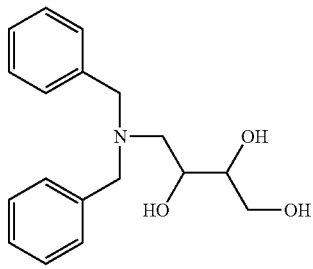

Was prepared according to EP675105(B1)

Preparation S

2-Dibenzylamino-1-(2,2-dimethyl-[1,3]-dioxolan-4-yl)-ethanol and {5-[(Dibenzylamino)-methyl]-2,2-dimethyl-[1,3]-dioxolan-4-yl}-methanol were prepared as a mixture

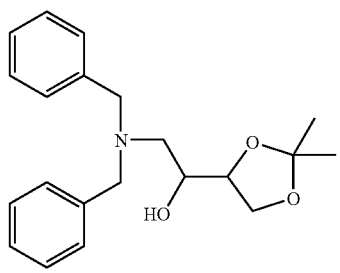

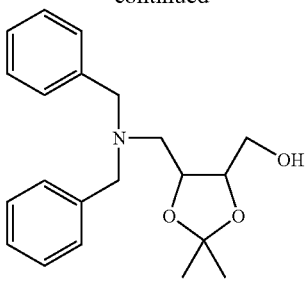

4-Dibenzylamino-butane-1,2,3-triol (10.0 g, 33.2 mmol) was dissolved in dry DMF (10 ml) and methanol (30 ml) and hydrogen chloride in dioxane (11 ml, 4N) was added. After 15 mins, methanol and excess hydrogen chloride were removed by evaporation at reduced pressure. Dimethoxypropane (4.0 g, 38.4 mmol) and para-toluenesulfonic acid (catalytic amount) were added and the mixture stirred for 18 h at ambient temperature. Triethylamine (0.5 ml) was added and solvents removed at reduced pressure. The residue did not dissolve in triethylamine (4-5 ml) so ethyl acetate (150 ml) was added and the solids filtered off. The filtrate was evaporated to give the crude product as an oil. The purified product mixture was obtained by chromatography on silica gel in combined yield of 8.18 g, 72%.

The structure was confirmed by Mass Spec (ESI) m/z: Calculated for $C_{21}H_{27}NO_3$ [M+H]$^+$341.454. Found 324.08

Preparation T

Acetic acid {3-chlorocarbonyl-5-[2-(2,2-dimethyl-[1,3]-dioxolan-4-yl)-2-hydroxy-ethylcarbamoyl]-2,4,6-triiodo-phenylcarbamoyl}-methyl ester and Acetic acid {3-chlorocarbonyl-5-[(5-hydroxymethyl-2,2-dimethyl-[1,3]-dioxolan-4-ylmethyl)-carbamoyl]-2,4,6-triiodo-phenylcarbamoyl}-methyl ester were prepared as a mixture

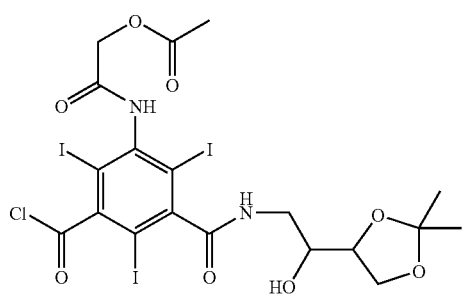

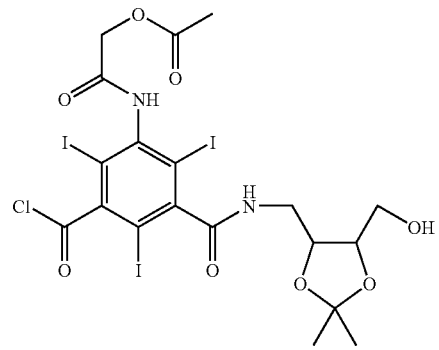

The mixture of 2-Dibenzylamino-1-(2,2-dimethyl-[1,3]dioxolan-4-yl)-ethanol and {5-[(Dibenzylamino)-methyl]-2,2-dimethyl-[1,3]dioxolan-4-yl}-methanol (2.32 g, 14.4 mmol) was dissolved in dimethylacetamide and triethylamine (4 ml, 28.8 mmol) added, followed by acetic acid (3,5-bis-chlorocarbonyl-2,4,6-triiodo-phenylcarbamoyl)-methyl ester (10.0 g, 14.4 mmol). The mixture was stirred at 40° C. for 24 h then cooled, diluted with ethyl acetate (150 ml) and washed with ice-water (4×30 ml), brine, dried over sodium sulphate, filtered and evaporated to give crude product as a solid foam. Pure product was obtained by chromatography on silica gel as a white solid foam (4.9 g, 42% yield).

The structure was confirmed by Mass Spec (ESI) m/z: Calculated for $C_{19}H_{20}Cl\ I_3N_2O_8$[M+H]$^+$820.546. Found 818.88

Example 1

N-(2,3-Dihydroxy-propyl)-N'-(3-{3-[(2,3-dihydroxy-propyl)-5-(2-hydroxy-acetylamino)-methyl-carbamoyl]-2,4,6-triiodo-benzoylamino}-propyl)-5-(2-hydroxy-acetylamino)-2,4,6-triiodo-N-methyl-isophthalamide

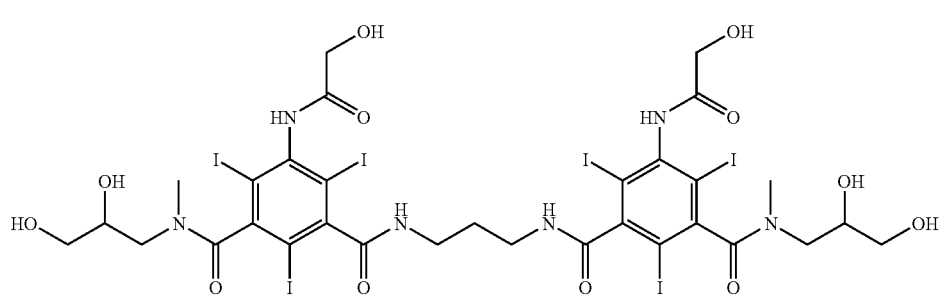

1,3-propanediamine (0.3 eq) and triethylamine (1.2 eq) were added to a solution of acetic acid {3-chlorocarbonyl-5-[(2,3-dihydroxy-propyl)-methyl-carbamoyl]-2,4,6-triiodo-phenylcarbamoyl}-methyl ester (2.5 g, 3.27 mmol) in DMA (5 mL). The reaction was stirred at ambient temperature until the reaction proceeds no further. The reaction mixture was extracted into ethyl actetate and washed with water to remove the DMA. The organic layer was dried over MgSO4 and the filtrate concentrated under vacuum to give the desired compound which was used in the next step without purification. The crude material was dissolved in the minimum amount of methanol and treated with aqueous ammonia. The reaction was stirred at ambient temperature and monitored by LC-MS. Whereupon, the reaction mixture was concentrated to dryness, dissolved in the minimum amount of water, filtered and purified by preparative HPLC to give the desired final product. Full deprotection could also be carried out by refluxing for 1 hour, the crude mixture in 2M aqueous HCl.

The structure was confirmed by Mass Spec (ESI) m/z: Calculated for $C_{31}H_{36}I_6N_6O_{12}$ [M]$^+$1446.06 Found 1446.49

Following the procedure of Example 1 the following symmetrical dimeric compounds of Examples 2 to 32 and 39 to 43 can be prepared:

Example 2

5-(2,3-Dihydroxy-propionylamino)-N-(2,3-dihydroxy-propyl)-N'-(3-{3-[(2,3-dihydroxy-propyl)-5-(2,3-Dihydroxy-propionylamino)-methyl-carbamoyl]-2,4,6-triiodo-benzoylamino}-propyl)-2,4,6-triiodo-N-methyl-isophthalamide

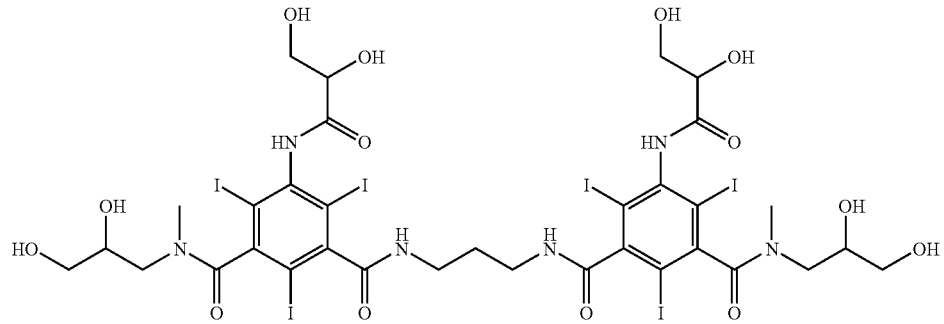

The structure was confirmed by Mass Spec (ESI) m/z: Calculated for $C_{33}H_{40}I_6N_6O_{14}$ [M]$^+$1506.11 Found 1506.81

Example 3

N-(2,3-Dihydroxy-propyl)-N'-(3-{3-[(2,3-dihydroxy-propyl)-5-(2,3,4-trihydroxy-butyrylamino)-methyl-carbamoyl]-2,4,6-triiodo-benzoylamino}-propyl)-2,4,6-triiodo-N-methyl-5-(2,3,4-trihydroxy-butyrylamino)-isophthalamide

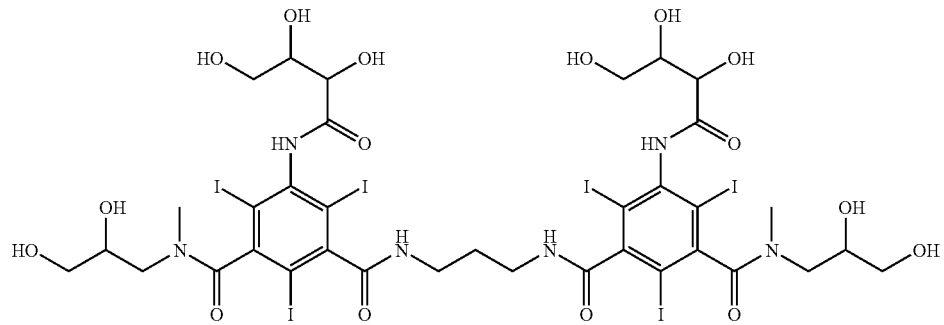

The structure was confirmed by Mass Spec (ESI) m/z: Calculated for $C_{35}H_{44}I_6N_6O_{16}$ [M]$^+$1566.198 Found 1566.88

Example 4

N-(2,3-Dihydroxy-propyl)-N'-{3-[3-(2,3-dihydroxy-propylcarbamoyl)-5-(2-hydroxy-acetylamino)-2,4,6-triiodo-benzoylamino]-propyl}-5-(2-hydroxy-acetylamino)-2,4,6-triiodo-isophthalamide

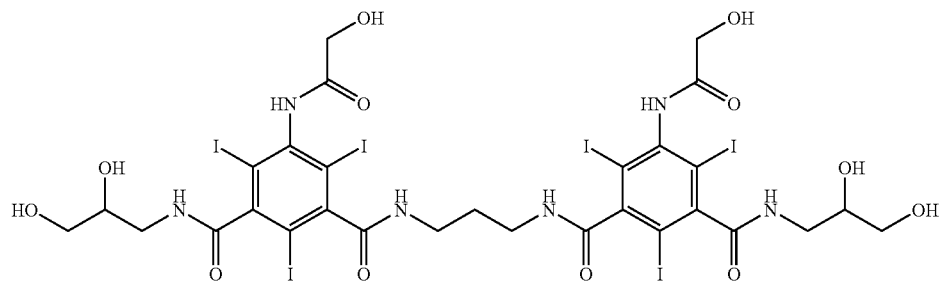

The structure was confirmed by Mass Spec (ESI) m/z: Calculated for $C_{29}H_{32}I_6N_6O_{12}$ $[M]^+$ 1418.038 Found 1418.83

Example 5

N-(2,3-Dihydroxy-propyl)-N'-(3-{3-[(2,3-dihydroxy-propyl)-(2-hydroxy-ethyl)-carbamoyl]-5-(2-hydroxy-acetylamino)-2,4,6-triiodo-benzoylamino}-propyl)-5-(2-hydroxy-acetylamino)-N-(2-hydroxy-ethyl)-2,4,6-triiodo-isophthalamide

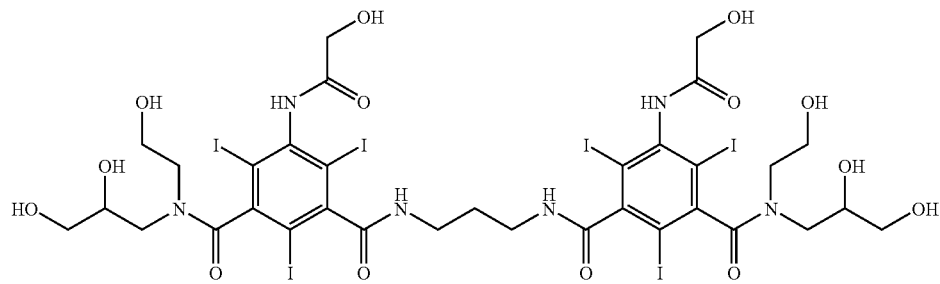

The structure was confirmed by Mass Spec (ESI) m/z: Calculated for $C_{33}H_{40}I_6N_6O_{14}$ $[M]^+$ 1506.11 Found 1506.71

Example 6

5-(2,3-Dihydroxy-propionylamino)-N-(2,3-dihydroxy-propyl)-N'-(3-{3-[(2,3-dihydroxy-propyl)-(2-hydroxy-ethyl)-carbamoyl]-5-(2,3-Dihydroxy-propionylamino)-2,4,6-triiodo-benzoylamino}-propyl)-N-(2-hydroxy-ethyl)-2,4,6-triiodo-isophthalamide

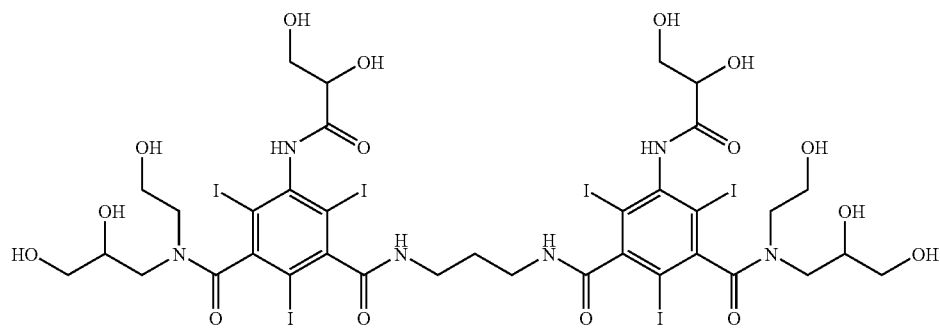

The structure was confirmed by Mass Spec (ESI) m/z: Calculated for $C_{35}H_{44}I_6N_6O_{16}$ $[M]^+$ 1566.16 Found 1566.71

Example 7

5-(2-Hydroxy-acetylamino)-2,4,6-triiodo-N-(2,3,4-trihydroxy-butyl)-N'-{5-(2-hydroxy-acetylamino)-3-[2,4,6-triiodo-3-(2,3,4-trihydroxy-butylcarbamoyl)-benzoylamino]-propyl}-isophthalamide

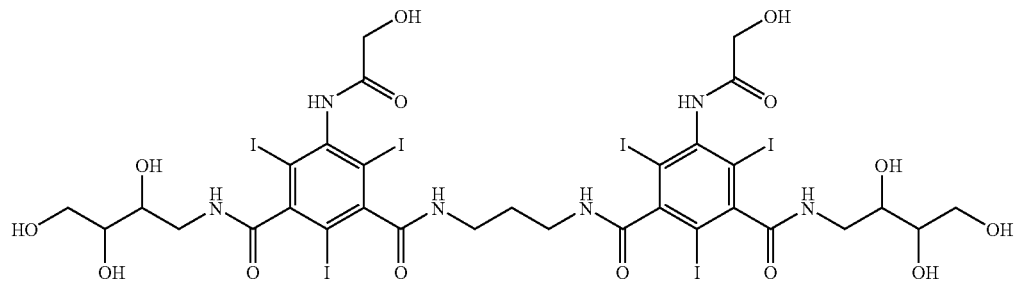

Example 8

N-(2,3-Dihydroxy-propyl)-N'-(3-{3-[(2,3-dihydroxy-propyl)-methyl-carbamoyl]-5-[(2-hydroxy-acetyl)-methyl-amino]-2,4,6-triiodo-benzoylamino}-propyl)-5-[(2-hydroxy-acetyl)-methyl-amino]-2,4,6-triiodo-N-methyl-isophthalamide

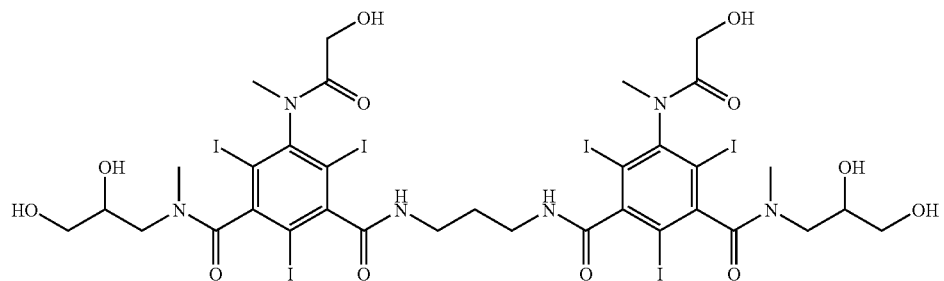

The structure was confirmed by Mass Spec (ESI) m/z: Calculated for $C_{33}H_{40}I_6N_6O_{12}$ $[M]^+$ 1474.11 Found 1474.64

Example 9

N-(2,3-Dihydroxy-propyl)-N'-[3-({3-[(2,3-dihydroxy-propyl)-5-(2-hydroxy-acetylamino)-methyl-carbamoyl]-2,4,6-triiodo-benzoyl}-methyl-amino)-propyl]-5-(2-hydroxy-acetylamino)-2,4,6-triiodo-N,N'-dimethyl-isophthalamide

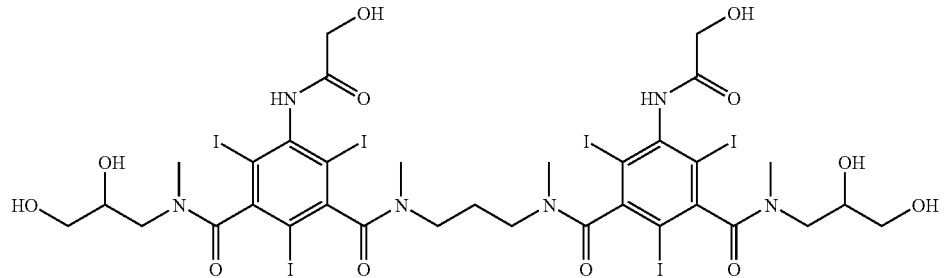

The structure was confirmed by Mass Spec (ESI) m/z: Calculated for $C_{33}H_{40}I_6N_6O_{12}$ $[M]^+$ 1474.11 Found 1474.80

Example 10

5-(2,3-Dihydroxy-propionylamino)-N-(2,3-dihydroxy-propyl)-N'-[3-({3-[(2,3-dihydroxy-propyl)-5-(2,3-dihydroxy-propionylamino)-methyl-carbamoyl]-2,4,6-triiodo-benzoyl}-methyl-amino)-propyl]-2,4,6-triiodo-N,N'-dimethyl-isophthalamide

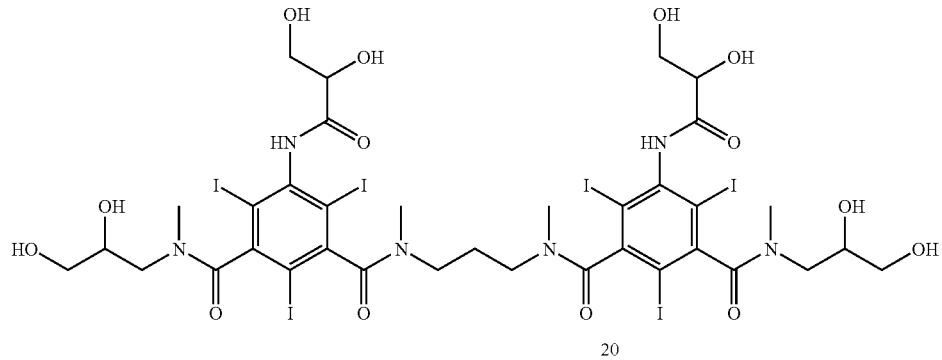

The structure was confirmed by Mass Spec (ESI) m/z:
Calculated for $C_{35}H_{44}I_6N_6O_{14}$ [M]$^+$1534.16 Found 1533.98

Example 11

N-(2,3-Dihydroxy-propyl)-N'-(3-{[3-(2,3-dihydroxy-propylcarbamoyl)-2,4,6-triiodo-benzoyl]-5-(2-hydroxy-acetylamino)-methyl-amino}-propyl)-5-(2-hydroxy-acetylamino)-2,4,6-triiodo-N'-methyl-isophthalamide

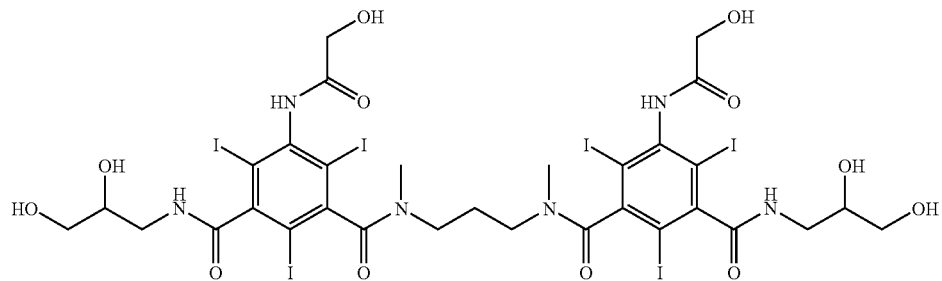

The structure was confirmed by Mass Spec (ESI) m/z:
Calculated for $C_{31}H_{36}I_6N_6O_{12}$[M]$^+$1446.06 Found 1446.87

Example 12

5-(2,3-Dihydroxy-propionylamino)-N-(2,3-dihydroxy-propyl)-N'-(3-{[3-(2,3-dihydroxy-propylcarbamoyl)-5-(2,3-dihydroxy-propionylamino)-2,4,6-triiodo-benzoyl]-methyl-amino}-propyl)-2,4,6-triiodo-N'-methyl-isophthalamide

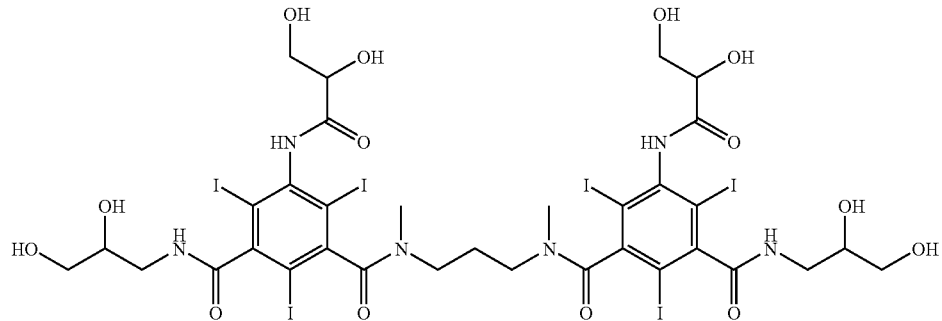

The structure was confirmed by Mass Spec (ESI) m/z:
Calculated for $C_{33}H_{40}I_6N_6O_{14}$ [M]$^+$1506.11 Found 1506.86

Example 13

N-(2,3-Dihydroxy-propyl)-N'-[3-({3-[(2,3-dihydroxy-propyl)-(2-hydroxy-ethyl)-carbamoyl]-5-(2-hydroxy-acetylamino)-2,4,6-triiodo-benzoyl}-methyl-amino)-propyl]-5-(2-hydroxy-acetylamino)-N-(2-hydroxy-ethyl)-2,4,6-triiodo-N'-methyl-isophthalamide

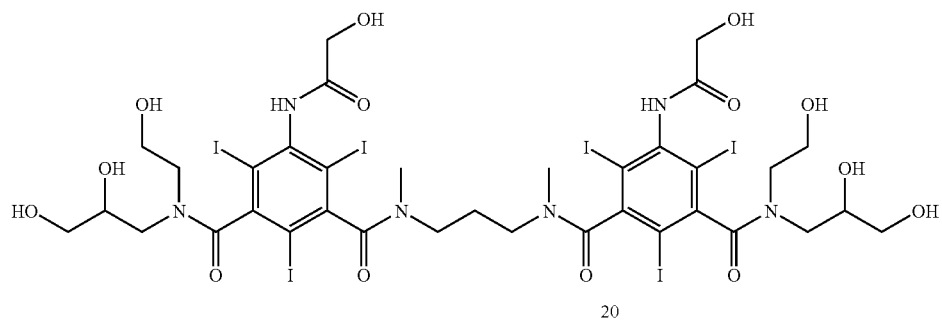

The structure was confirmed by Mass Spec (ESI) m/z: Calculated for $C_{35}H_{44}I_6N_6O_{14}$ $[M]^+$ 1534.16 Found 1534.75

Example 14

5-(2,3-Dihydroxy-propionylamino)-N-(2,3-dihydroxy-propyl)-N'-[3-({3-[(2,3-dihydroxy-propyl)-(2-hydroxy-ethyl)-carbamoyl]-5-(2,3-Dihydroxy-propionylamino)-2,4,6-triiodo-benzoyl}-methyl-amino)-propyl]-N-(2-hydroxy-ethyl)-2,4,6-triiodo-N'-methyl-isophthalamide

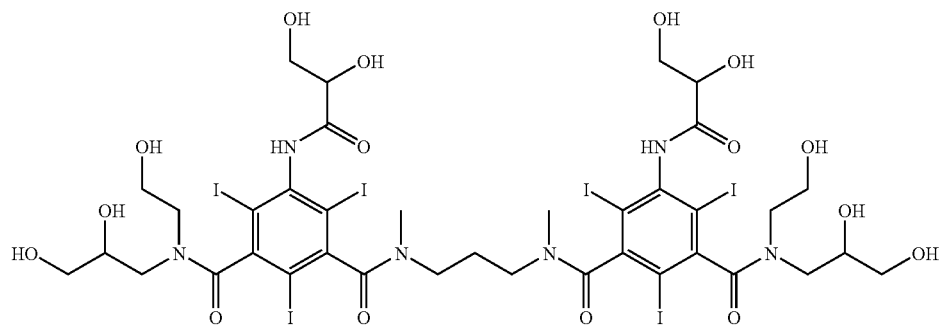

The structure was confirmed by Mass Spec (ESI) m/z: Calculated for $C_{37}H_{48}I_6N_6O_{16}$ $[M]^+$ 1594.21 Found 1594.75

Example 15

N-(2,3-Dihydroxy-propyl)-N'-[3-({3-[(2,3-dihydroxy-propyl)-methyl-carbamoyl]-5-[(2-hydroxy-acetyl)-methyl-amino]-2,4,6-triiodo-benzoyl}-methyl-amino)-propyl]-5-[(2-hydroxy-acetyl)-methyl-amino]-2,4,6-triiodo-N,N'-dimethyl-isophthalamide

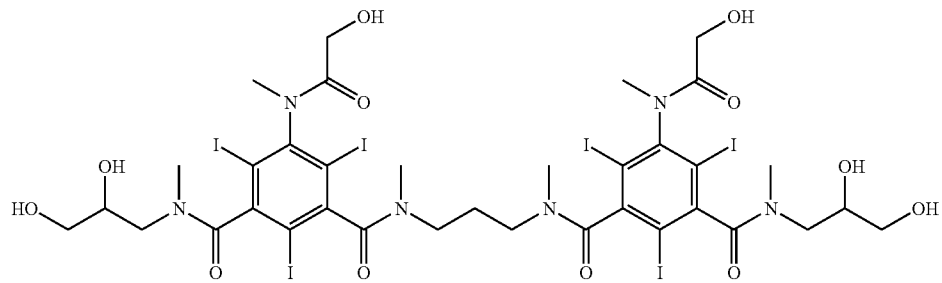

The structure was confirmed by Mass Spec (ESI) m/z: Calculated for $C_{35}H_{44}I_6N_6O_{12}$ $[M]^+$ 1502.16 Found 1502.76

Example 16

N-(2,3-Dihydroxy-propyl)-N'-(3-{3-[(2,3-dihydroxy-propyl)-methyl-carbamoyl]-5-(2-hydroxy-acetylamino)-2,4,6-triiodo-benzoylamino}-propyl)-5-(2-hydroxy-acetylamino)-2,4,6-triiodo-N,N'-dimethyl-isophthalamide

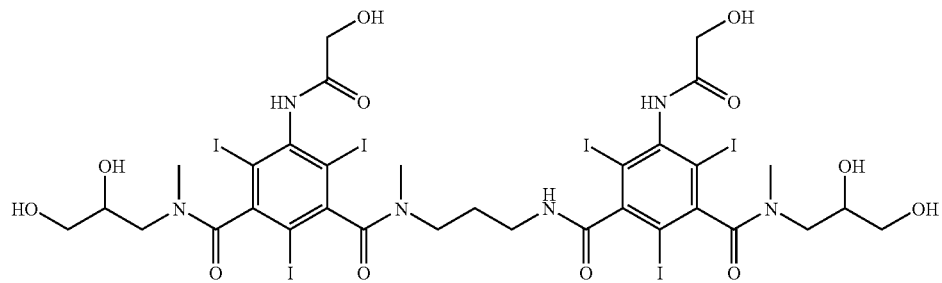

The structure was confirmed by Mass Spec (ESI) m/z: Calculated for $C_{32}H_{38}I_6N_6O_{12}$ [M]$^+$ 1460.08 Found 1462.84

Example 17

5-(2,3-Dihydroxy-propionylamino)-N-(2,3-dihydroxy-propyl)-N'-(4-{3-[(2,3-dihydroxy-propyl)-methyl-carbamoyl]-5-(2,3-dihydroxy-propionylamino)-2,4,6-triiodo-benzoylamino}-butyl)-2,4,6-triiodo-N-methyl-isophthalamide

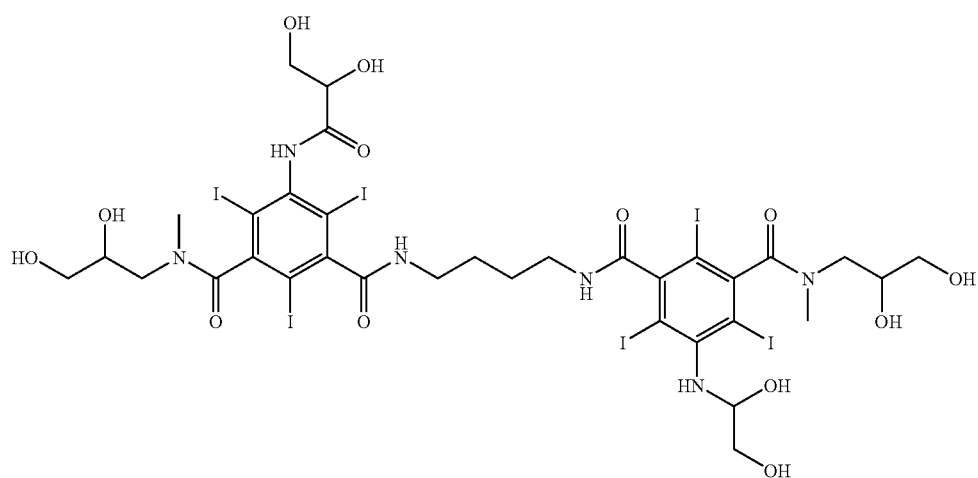

The structure was confirmed by Mass Spec (ESI) m/z: Calculated for $C_{33}H_{42}I_6N_6O_{12}$ [M]$^+$ 1520.13 Found 1520.7

Example 18

N-(2,3-Dihydroxy-propyl)-N'-{4-[3-(2,3-dihydroxy-propylcarbamoyl)-2,4,6-triiodo-5-(2,3,4-trihydroxy-butyrylamino)-benzoylamino]-butyl}-2,4,6-triiodo-5-(2,3,4-trihydroxy-butyrylamino)-isophthalamide

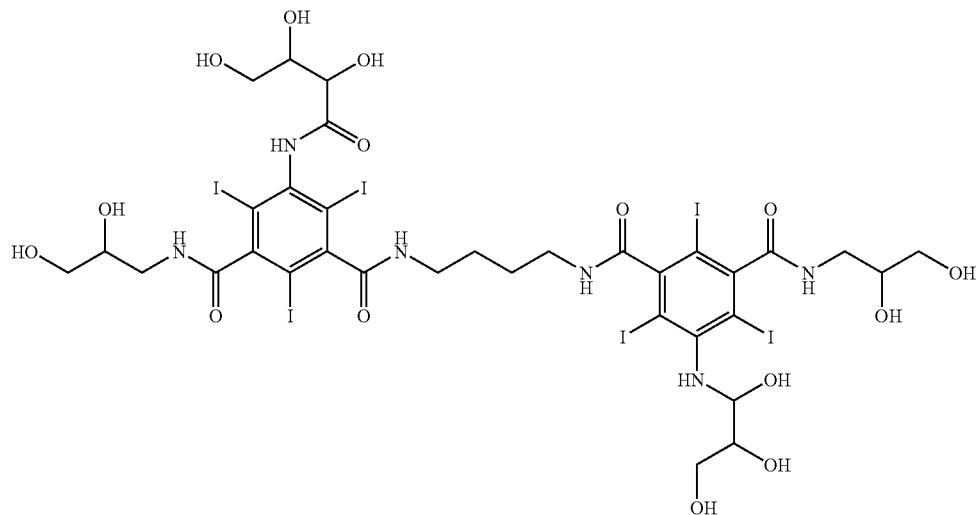

The structure was confirmed by Mass Spec (ESI) m/z: Calculated for $C_{33}H_{42}I_6N_6O_{15}$ $[M]^+$ 1552.13 Found 1552.6

Example 19

5-(2,3-Dihydroxy-propionylamino)-N-(2,3-dihydroxy-propyl)-N'-(5-{3-[(2,3-dihydroxy-propyl)-methyl-carbamoyl]-5-(2,3-dihydroxy-propionylamino)-2,4,6-triiodo-benzoylamino}-pentyl)-2,4,6-triiodo-N-methyl-isophthalamide

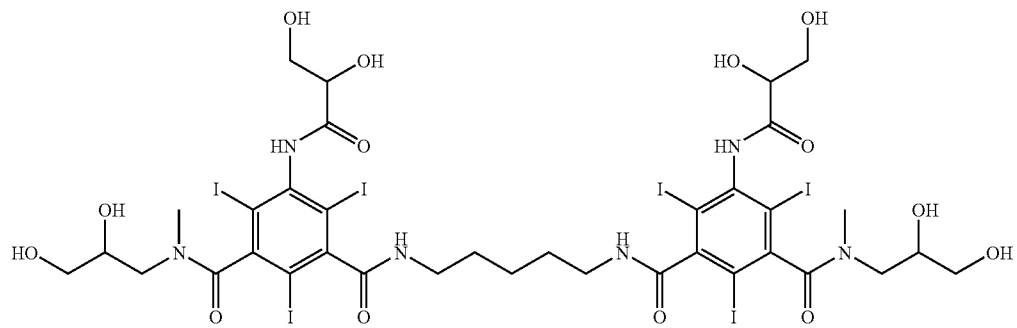

The structure was confirmed by Mass Spec (ESI) m/z: Calculated for $C_{35}H_{44}I_6N_6O_{14}$ $[M]^+$ 1534.16 Found 1534.6

Example 20

5-(2,3-Dihydroxy-propionylamino)-N-(2,3-dihydroxy-propyl)-N'-(6-{3-[(2,3-dihydroxy-propyl)-methyl-carbamoyl]-5-(2,3-dihydroxy-propionylamino)-2,4,6-triiodo-benzoylamino}-hexyl)-2,4,6-triiodo-N-methyl-isophthalamide

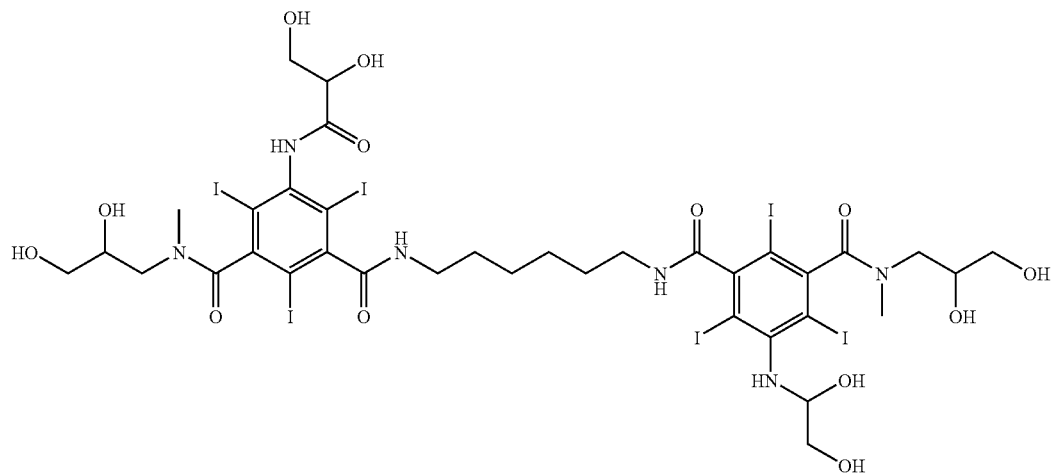

The structure was confirmed by Mass Spec (ESI) m/z: Calculated for $C_{35}H_{46}I_6N_6O_{13}$ $[M]^+$ 1548.18 Found 1548.7

Example 21

N-(2,3-Dihydroxy-propyl)-N'-{2-[2-({3-[(2,3-dihydroxy-propyl)-methyl-carbamoyl]-5-(2-hydroxy-acetylamino)-2,4,6-triiodo-benzoyl}-methyl-amino)-ethoxy]-ethyl}-5-(2-hydroxy-acetylamino)-2,4,6-triiodo-N,N'-dimethyl-isophthalamide

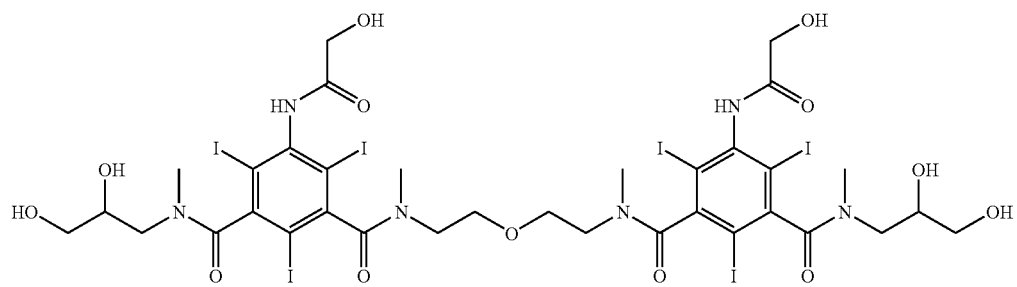

The structure was confirmed by Mass Spec (ESI) m/z: Calculated for $C_{34}H_{42}I_6N_6O_{13}$ $[M]^+$ 1504.13 Found 1504.6

Example 22

N-(2,3-Dihydroxy-propyl)-N'-{2-[2-(2-{3-[(2,3-dihydroxy-propyl)-methyl-carbamoyl]-5-(2-hydroxy-acetylamino)-2,4,6-triiodo-benzoylamino}-ethoxy)-ethoxy]-ethyl}-5-(2-hydroxy-acetylamino)-2,4,6-triiodo-N-methyl-isophthalamide

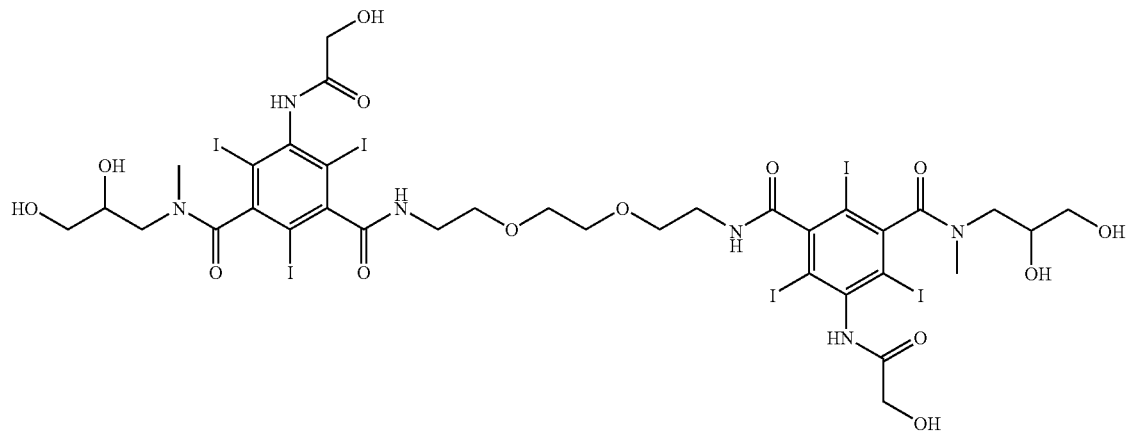

The structure was confirmed by Mass Spec (ESI) m/z: Calculated for $C_{34}H_{42}I_6N_6O_{14}$ $[M]^+$ 1520.13 Found 1521.0

Example 23

5-(2,3-Dihydroxy-propionylamino)-N-(2,3-dihydroxy-propyl)-N'-{2-[2-(2-{3-[(2,3-dihydroxy-propyl)-methyl-carbamoyl]-5-(2,3-dihydroxy-propionylamino)-2,4,6-triiodo-benzoylamino}-ethoxy)-ethoxy]-ethyl}-2,4,6-triiodo-N-methyl-isophthalamide

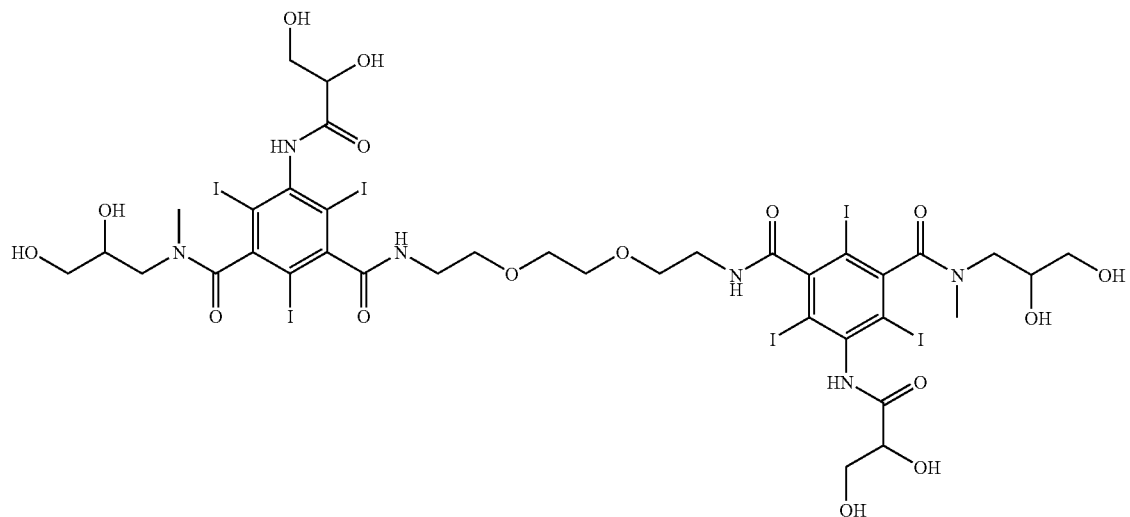

The structure was confirmed by Mass Spec (ESI) m/z: Calculated for $C_{36}H_{46}I_6N_6O_{16}$ $[M]^+$ 1580.19 Found 1580.9

Example 24

N-(2,3-Dihydroxy-propyl)-3-(4-{3-[(2,3-dihydroxy-propyl)-methyl-carbamoyl]-5-(2-hydroxy-acetylamino)-2,4,6-triiodo-benzoyl}-piperazine-1-carbonyl)-5-(2-hydroxy-acetylamino)-2,4,6-triiodo-N-methyl-benzamide

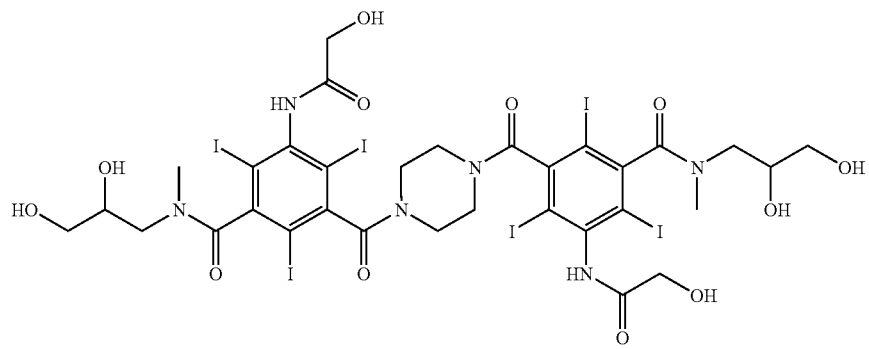

The structure was confirmed by Mass Spec (ESI) m/z: Calculated for $C_{32}H_{36}I_6N_6O_{12}$ $[M]^+$ 1458.07 Found 1458.77

Example 25

3-(2,3-Dihydroxy-propionylamino)-N-(2,3-dihydroxy-propyl)-5-(4-{3-[(2,3-dihydroxy-propyl)-methyl-carbamoyl]-3-(2,3-dihydroxy-propionylamino)-2,4,6-triiodo-benzoyl}-piperazine-1-carbonyl)-2,4,6-triiodo-N-methyl-benzamide

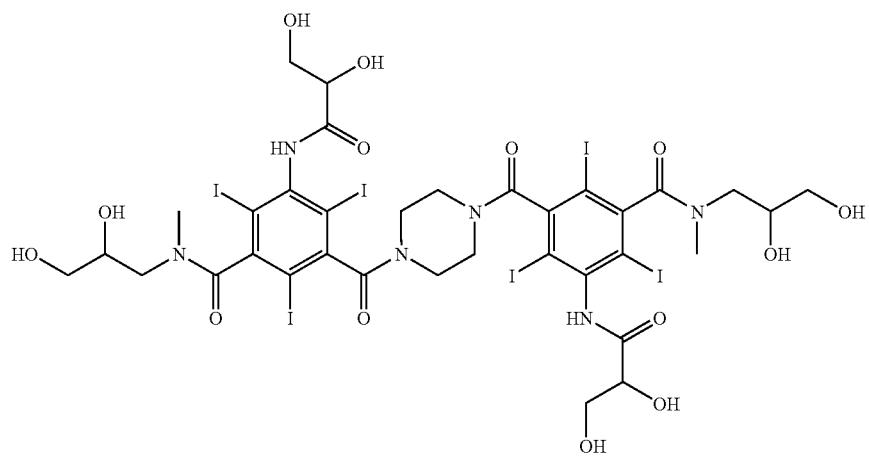

The structure was confirmed by Mass Spec (ESI) m/z: Calculated for $C_{34}H_{40}I_6N_6O_{14}$ $[M]^+$ 1518.15 Found 1518.83

Example 26

N-(2,3-Dihydroxy-propyl)-3-{-4-[3-(2,3-dihydroxy-propylcarbamoyl)-5-(2-hydroxy-acetylamino)-2,4,6-triiodo-benzoyl]-piperazine-1-carbonyl}-5-(2-hydroxy-acetylamino)-2,4,6-triiodo-benzamide

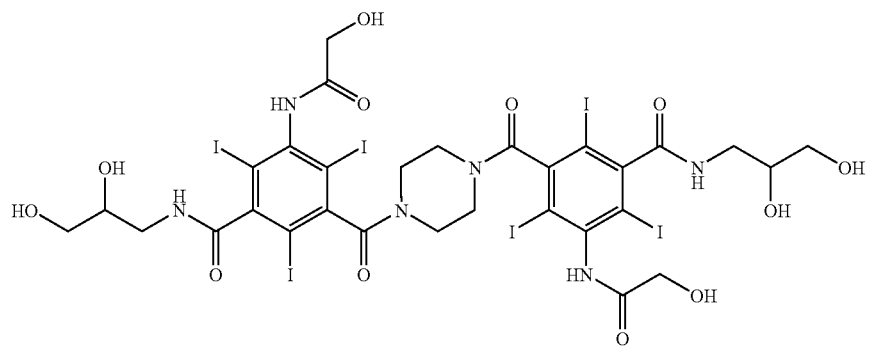

The structure was confirmed by Mass Spec (ESI) m/z: Calculated for $C_{30}H_{32}I_6N_6O_{12}$ $[M]^+$ 1430.01 Found 1430.67

Example 27

N-(2,3-Dihydroxy-propyl)-N'-(4-{3-[(2,3-dihydroxy-propyl)-methyl-carbamoyl]-5-(2-hydroxy-acetylamino)-2,4,6-triiodo-benzoylamino}-cyclohexyl)-5-(2-hydroxy-acetylamino)-2,4,6-triiodo-N-methyl-isophthalamide

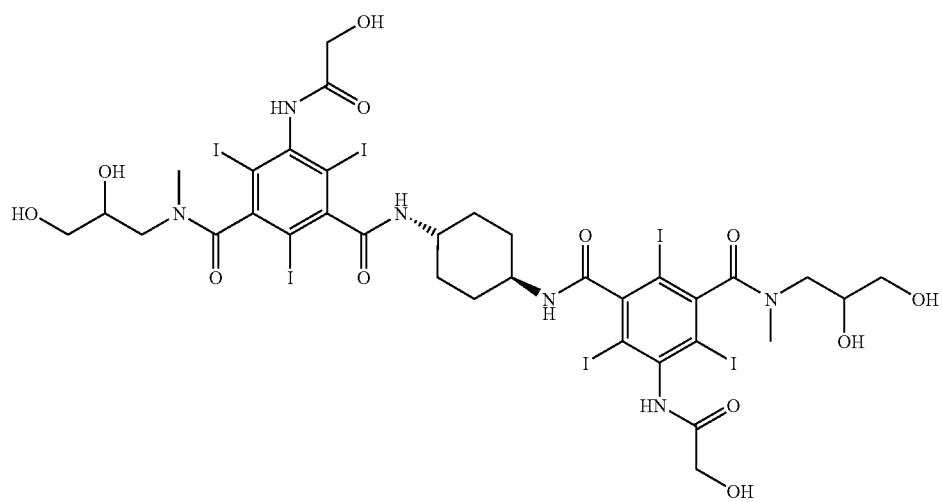

The structure was confirmed by Mass Spec (ESI) m/z: Calculated for $C_{34}H_{40}I_6N_6O_{12}$ $[M]^+$ 1486.12 Found 1486.8

Example 28

5-(2,3-Dihydroxy-propionylamino)-N-(2,3-dihydroxy-propyl)-N'-(4-{3-[(2,3-dihydroxy-propyl)-methyl-carbamoyl]-5-(2,3-dihydroxy-propionylamino)-2,4,6-triiodo-benzoylamino}-cyclohexyl)-2,4,6-triiodo-N-methyl-isophthalamide

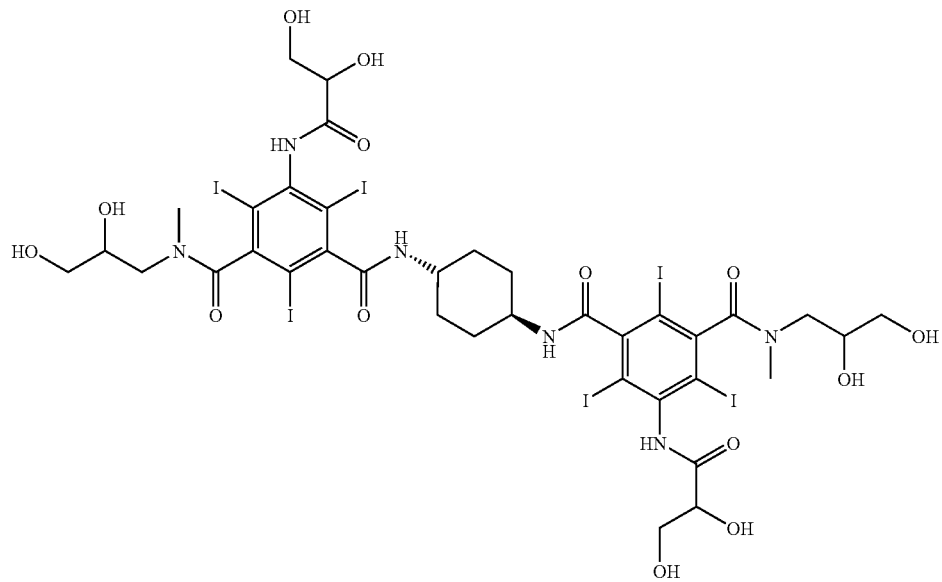

The structure was confirmed by Mass Spec (ESI) m/z: Calculated for $C_{36}H_{44}I_6N_6O_{14}$ $[M]^+$ 1546.17 Found 1546.7

Example 29

N-(2,3-Dihydroxy-propyl)-N'-(3-{3-[(2,3-dihydroxy-propyl)-methyl-carbamoyl]-5-(2-hydroxy-acetylamino)-2,4,6-triiodo-benzoylamino}-propyl)-5-(2-hydroxy-acetylamino)-N'-(2-hydroxy-ethyl)-2,4,6-triiodo-N-methyl-isophthalamide

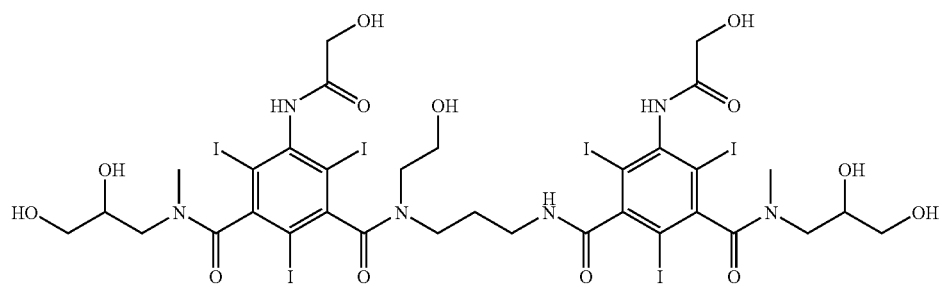

The structure was confirmed by Mass Spec (ESI) m/z: Calculated for $C_{33}H_{40}I_6N_6O_{13}$ $[M]^+$ 1490.11 Found 1490.91

Example 30

5-(2,3-Dihydroxy-propionylamino)-N-(2,3-dihydroxy-propyl)-N'-(3-{3-[(2,3-dihydroxy-propyl)-methyl-carbamoyl]-5-(2,3-dihydroxy-propionylamino)-2,4,6-triiodo-benzoylamino}-propyl)-N'-(2-hydroxy-ethyl)-2,4,6-triiodo-N-methyl-isophthalamide

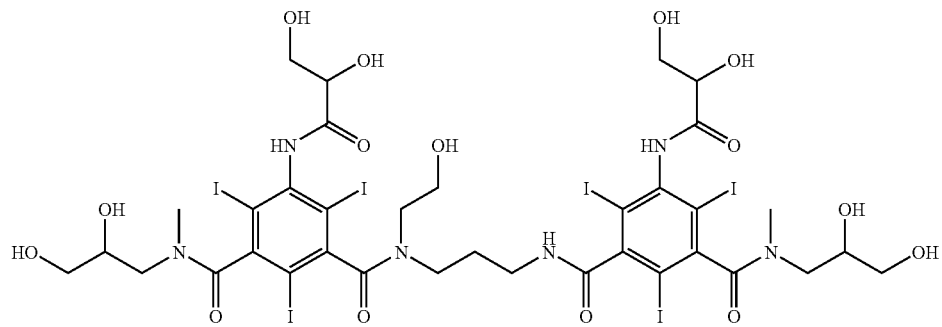

The structure was confirmed by Mass Spec (ESI) m/z:
Calculated for $C_{35}H_{44}I_6N_6O_{15}$ [M]$^+$1550.16 Found 1551.81

Example 31

N,N'-Bis-(2,3-dihydroxy-propyl)-N-{3-[3-(2,3-dihydroxy-propylcarbamoyl)-5-(2-hydroxy-acetylamino)-2,4,6-triiodo-benzoylamino]-propyl}-5-(2-hydroxy-acetylamino)-2,4,6-triiodo-isophthalamide

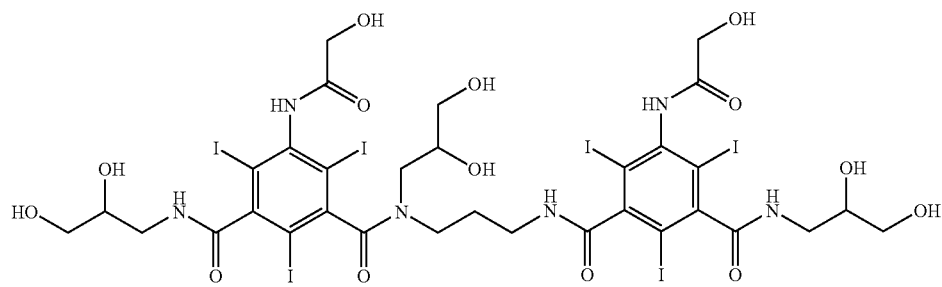

The structure was confirmed by Mass Spec (ESI) m/z:
Calculated for $C_{32}H_{38}I_6N_6O_{14}$ [M]$^+$1492.08 Found 1492.73

Example 32

N-(2,3-Dihydroxy-propyl)-N'-{1-[3-(2,3-dihydroxy-propylcarbamoyl)-5-(2-hydroxy-acetylamino)-2,4,6-triiodo-benzoyl]-piperidin-4-yl}-5-(2-hydroxy-acetylamino)-2,4,6-triiodo-isophthalamide

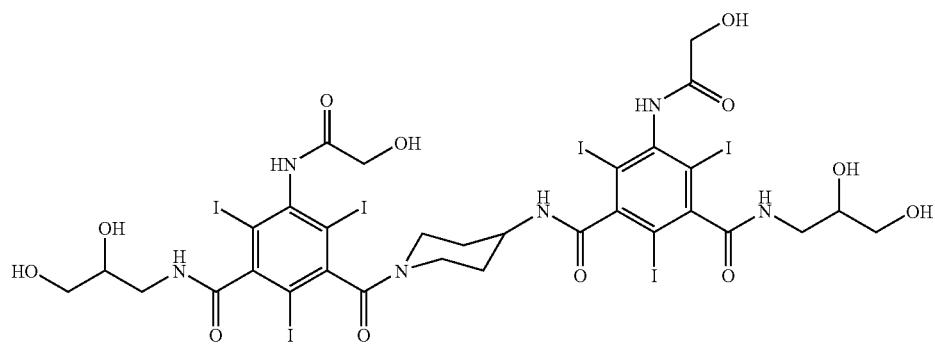

The structure was confirmed by Mass Spec (ESI) m/z:
Calculated for $C_{32}H_{38}I_6N_6O_{14}$ [M]$^+$1444.076 Found 1444.63

Example 33

5-(2-Hydroxy-acetylamino)-N-(2-hydroxy-1-hydroxymethyl-ethyl)-N'-{3-[3-(2-hydroxy-1-hydroxymethyl-ethylcarbamoyl)-5-(2-Hydroxy-acetylamino)-2,4,6-triiodo-benzoylamino]-propyl}-2,4,6-triiodo-isophthalamide

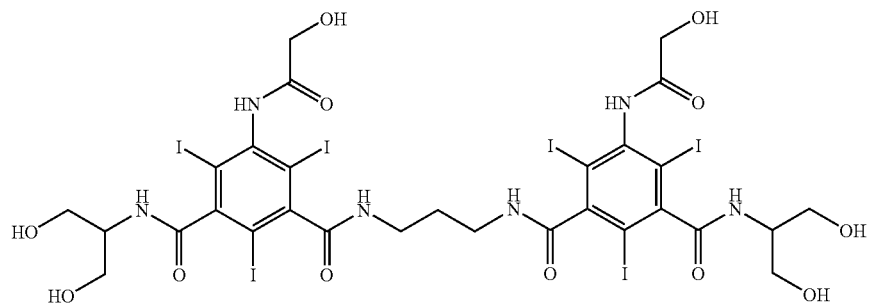

Acetic acid 3-acetoxy-2-[3-(2-acetoxy-acetylamino)-5-chlorocarbonyl-2,4,6-triiodo-benzoylamino]-propyl ester (2.0 g, 2.4 mmol) was dissolved in dimethylacetamide (15 ml) and 1,3-diaminopropane (70 mg, 1.0 mmol) and triethylamine (0.33 ml, 2.4 mmol) added. The solution was stirred at ambient temperature for 24 h then diluted with ethylacetate (150 ml) and washed with ice-water (4×30 ml). The product was washed out into the aqueous phase and this was evaporated to give crude product (1.5 g). The structure was confirmed by Mass Spec (ESI) m/z: Calculated for $C_{41}H_{44}I_6N_6O_{18}$ [M]$^+$1670.26 Found 1640.86

The crude Acetic acid 3-acetoxy-2-[3-{3-[3-(2-acetoxy-1-acetoxymethyl-ethylcarbamoyl)-5-(2-acetoxy-acetylamino)-2,4,6-triiodo-benzoylamino]-propylcarbamoyl}-5-(2-acetoxy-acetylamino)-2,4,6-triiodo-benzoylamino]-propyl ester (1.5 g) was dissolved in methanol (10 ml) and water (10 ml) was added. Concentrated aqueous ammonia (3 ml) was added and the solution stirred at ambient temperature for 18 h. The reaction was evaporated to dryness, the residue dissolved in water and purified by preparative hplc to give the title product as a white solid after freeze drying.

The structure was confirmed by Mass Spec (ESI) m/z: Calculated for $C_{29}H_{32}I_6N_6O_{12}$ [M]$^+$1418.04 Found 1418.65

Following the procedure of Example 33, dimeric compounds can be prepared, including those of Example 34.

Example 34

5-(2-Hydroxy-acetylamino)-N-(2-hydroxy-1-hydroxymethyl-ethyl)-N'-(3-{[3-(2-hydroxy-1-hydroxymethyl-ethylcarbamoyl)-5-(2-Hydroxy-acetylamino)-2,4,6-triiodo-benzoyl]-methyl-amino}-propyl)-2,4,6-triiodo-N'-methyl-isophthalamide

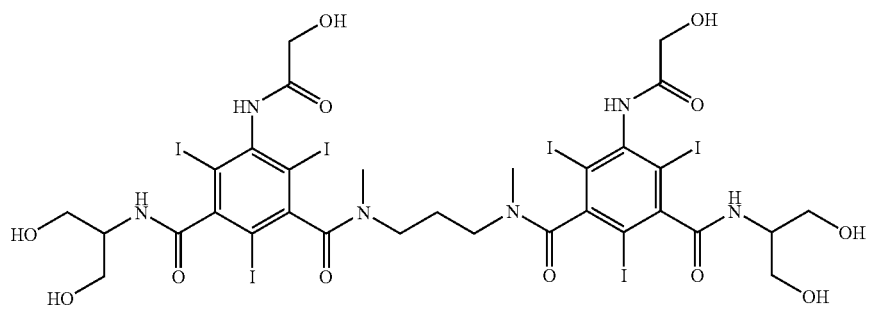

The structure was confirmed by Mass Spec (ESI) m/z: Calculated for $C_{31}H_{36}I_6N_6O_{12}$ [M]$^+$1446.06 Found 1446.67

Example 35

5-(2-Hydroxy-acetylamino)-N-(2-hydroxy-1,1-bis-hydroxymethyl-ethyl)-N'-{3-[3-(2-hydroxy-1,1-bis-hydroxymethyl-ethylcarbamoyl)-5-(2-hydroxy-acetylamino)-2,4,6-triiodo-benzoylamino]-propyl}-2,4,6-triiodo-isophthalamide

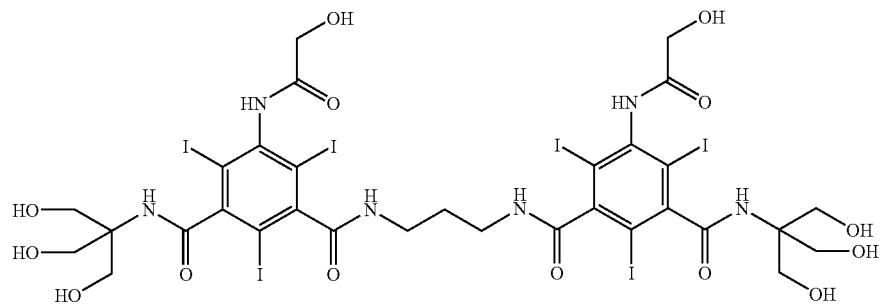

(5-Amino-2,2-dimethyl-[1,3]dioxan-5-yl)-methanol (9.5 g, 58.9 mmol) was dissolved in dimethylacetamide (100 ml) and triethylamine (2 ml) added. Acetic acid (3,5-bis-chlorocarbonyl-2,4,6-triiodo-phenylcarbamoyl)-methyl ester (21.0 g, 30.2 mmol) was added and the mixture heated under nitrogen at 60° C. for 24 h. On cooling, ethyl acetate (1.2 l) was added and the solution washed with ice-water (4×120 ml), brine, dried over sodium sulphate, filtered and evaporated to give the crude product. The pure product obtained as a white solid by chromatography on silica gel (8.32 g, 34% yield). The product was then fully deprotected after reflux for 1 hour in a 1:1 mixture of 2M aqueous HCl and MeOH, whereupon, the reaction mixture was concentrated to dryness, dissolved in the minimum amount of water, filtered and purified by preparative HPLC to give the desired final product.

The structure was confirmed by Mass Spec (ESI) m/z: Calculated for $C_{31}H_{30}I_6N_6O_{14}$ $[M]^+$ 1478.091 Found 1478.84

Example 36

N-(2,3-Dihydroxy-propyl)-N'-(3-{3-[(2,3-dihydroxy-propyl)-methyl-carbamoyl]-5-(2-hydroxy-acetylamino)-2,4,6-triiodo-benzoylamino}-propyl)-2,4,6-triiodo-N-methyl-5-(2,3,4-trihydroxy-butyrylamino)-isophthalamide 1,3-Propanediamine (1 eq) and triethylamine (2 eq) were added to a solution of acetic acid {3-chlorocarbonyl-5-[(2,3-dihydroxy-propyl)-methyl-carbamoyl]-2,4,6-triiodo-phenylcarbamoyl}-methyl ester (1 eq) in DMA (100 mL). The reaction was stirred at ambient temperature overnight. A solution of acetic acid 2,3-diacetoxy-1-{3-chlorocarbonyl-5-[(2,3-dihydroxy-propyl)-methyl-carbamoyl]-2,4,6-triiodo-phenylcarbamoyl}-propyl ester (1 eq) in DMA (2 mL) was added and the mixture was heated at 40° C. for two days. The reaction mixture was extracted into ethyl actetate and washed with water to remove the DMA. The organic layer was dried over MgSO₄ and the filtrate concentrated under vacuum to give the desired compound which was used in the next step without purification. The crude material was dissolved in the minimum amount of methanol and treated with aqueous ammonia. The reaction was stirred at ambient temperature and monitored by LC-MS. Whereupon, the reaction mixture was concentrated to dryness, dissolved in the minimum amount of water, filtered and purified by preparative HPLC to give the desired final product.

The structure was confirmed by Mass Spec (ESI) m/z: Calculated for $C_{33}H_{40}I_6N_6O_{14}$ $[M]^+$ 1506.11 Found 1506.74

Following the procedure of Example 36, unsymmetrical dimeric compounds can be prepared, including those of Examples 37 and 38.

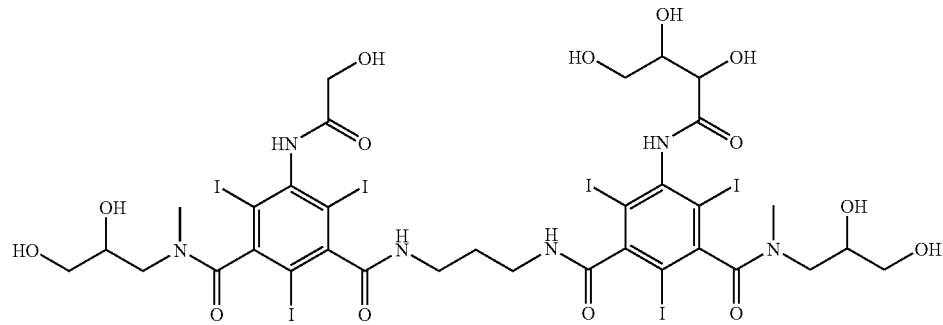

Example 37

5-(2,3-Dihydroxy-propionylamino)-N-(2,3-dihydroxy-propyl)-N'-(3-{3-[(2,3-dihydroxy-propyl)-methyl-carbamoyl]-5-(2-hydroxy-acetylamino)-2,4,6-triiodo-benzoylamino}-propyl)-2,4,6-triiodo-N-methyl-isophthalamide

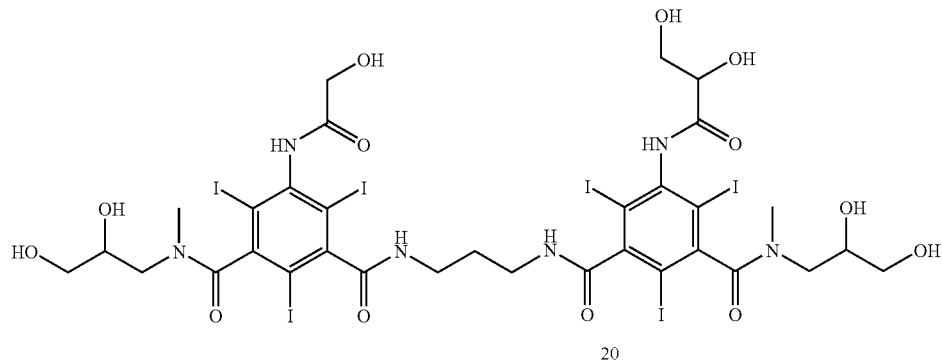

The structure was confirmed by Mass Spec (ESI) m/z: Calculated for $C_{32}H_{38}I_6N_6O_{13}$ $[M]^+$ 1476.08 Found 1476.76

Example 38

N-(2,3-Dihydroxy-propyl)-N'-(3-{3-[(2,3-dihydroxy-propyl)-methyl-carbamoyl]-5-(2,3-dihydroxy-propionylamino)-2,4,6-triiodo-benzoylamino}-propyl)-2,4,6-triiodo-N-methyl-5-(2,3,4-trihydroxy-butyrylamino)-isophthalamide

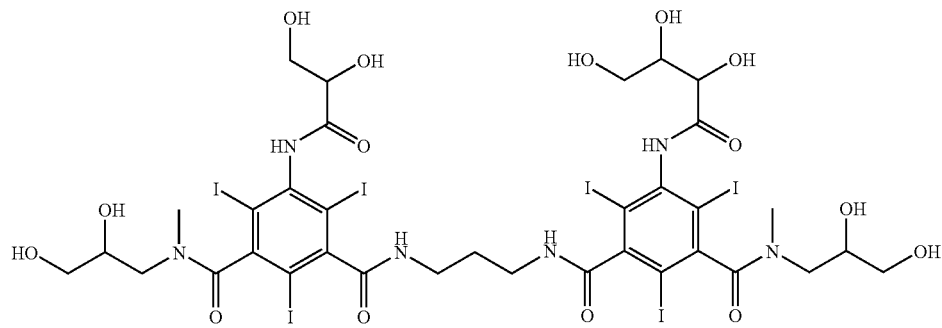

The structure was confirmed by Mass Spec (ESI) m/z: Calculated for $C_{34}H_{42}I_6N_6O_{15}$ $[M]^+$ 1536.13 Found 1536.81

Example 39

5-(2,3-Dihydroxy-propionylamino)-N-(2,3-dihydroxy-propyl)-N'-{3-[3-(2,3-dihydroxy-propylcarbamoyl)-5-(2,3-dihydroxy-propionylamino)-2,4,6-triiodo-benzoylamino]-propyl}-2,4,6-triiodo-isophthalamide

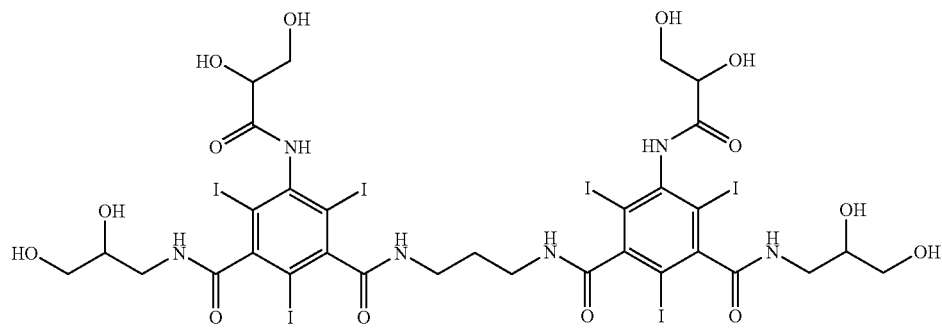

The structure was confirmed by Mass Spec (ESI) m/z: Calculated for $C_{31}H_{36}I_6N_6O_{14}$ $[M]^+$ 1478.05 Found 1478.83

Example 40

5-(2,3-Dihydroxy-propionylamino)-N-(2,3-dihydroxy-propyl)-N'-{5-[3-(2,3-dihydroxy-propylcarbamoyl)-5-(2,3-dihydroxy-propionylamino)-2,4,6-triiodo-benzoylamino]-pentyl}-2,4,6-triiodo-isophthalamide

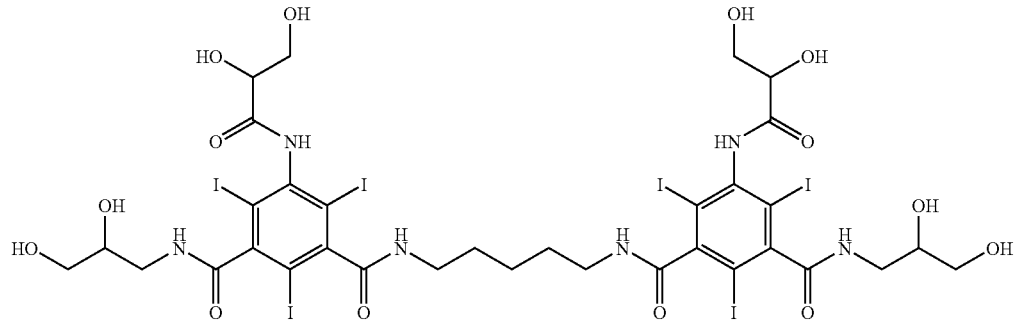

The structure was confirmed by Mass Spec (ESI) m/z: Calculated for $C_{33}H_{40}I_6N_6O_{14}$ [M]$^+$1506.11 Found 1506.82

Example 41

N-(2,3-Dihydroxy-propyl)-N'-{3-[[3-(2,3-dihydroxy-propylcarbamoyl)-5-(2-hydroxy-acetylamino)-2,4,6-triiodo-benzoyl]-(2-hydroxy-ethyl)-amino]-propyl}-5-(2-hydroxy-acetylamino)-2,4,6-triiodo-isophthalamide

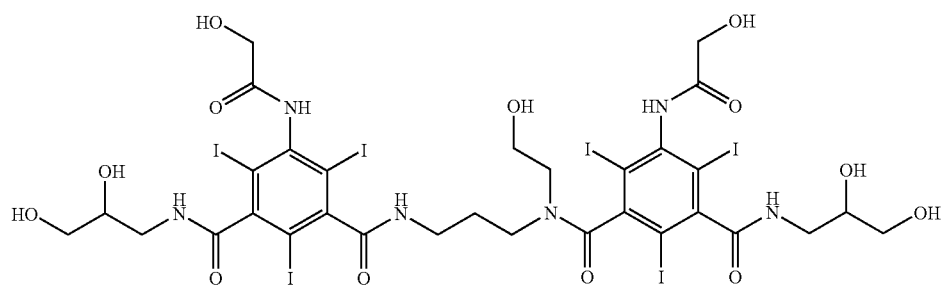

The structure was confirmed by Mass Spec (ESI) m/z: Calculated for $C_{31}H_{36}I_6N_6O_{13}$ [M]$^+$1462.05 Found 1462.66

Example 42

3-(2,3-Dihydroxy-propionylamino)-N-(2,3-dihydroxy-propyl)-5-{4-[3-(2,3-dihydroxy-propylcarbamoyl)-3-(2,3-dihydroxy-propionylamino)-2,4,6-triiodo-benzoyl]-piperazine-1-carbonyl}-2,4,6-triiodo-benzamide

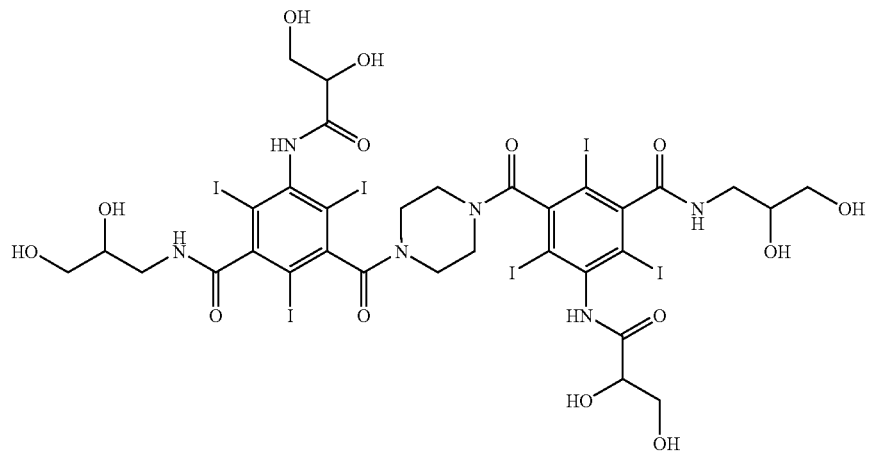

The structure was confirmed by Mass Spec (ESI) m/z: Calculated for $C_{32}H_{36}I_6N_6O_{14}$ $[M]^+$ 1490.06 Found 1490.74

Example 43

N-(2,3-Dihydroxy-propyl)-N'-{3-[3-(2,3-dihydroxy-propylcarbamoyl)-5-(2-hydroxy-acetylamino)-2,4,6-triiodo-benzoylamino]-propyl}-5-(2-hydroxy-acetylamino)-2,4,6-triiodo-N'-methyl-isophthalamide

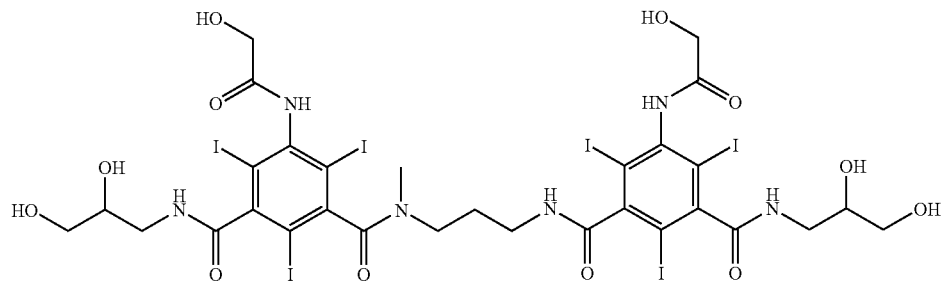

The structure was confirmed by Mass Spec (ESI) m/z: Calculated for $C_{30}H_{34}I_6N_6O_{12}$ $[M]^+$ 1432.03 Found 1433.29

What is claimed is:
1. Compounds of formula (I)

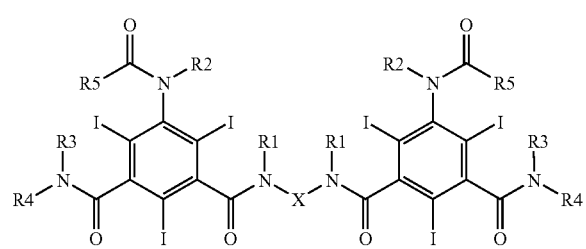

Formula (I)

and salts or optical active isomers thereof, wherein each $R^1$ independently are the same or different and denotes a hydrogen atom or a $C_1$ to $C_4$ straight or branched alkyl group which is optionally substituted by 1 to 4 —OH groups;

each of $R^2$ independently are the same or different and denote a hydrogen atom or a $C_1$ to $C_4$ straight or branched alkyl group;

each $R^3$ independently are the same or different and denotes a hydrogen atom or a $C_1$ to $C_4$ straight or branched alkyl group which is optionally substituted by 1 to 4 —OH groups;

each $R^4$ independently are the same or different and denote $C_1$ to $C_6$ straight or branched alkyl moieties substituted by up to 6 —OH groups; and each $R^5$ independently are the same or different and denote $C_1$ to $C_6$ straight or branched alkyl moieties substituted by up to 6 —OH groups; and X denotes a 1,4-cyclohexylene group, or X together with the adjacent —$NR^1$ groups forms a 1,4-piperazine group or a 4-aminopiperidine group.

2. Compound as claimed in claim 1 wherein each of the $R^1$ substituents denote a hydrogen atom, a methyl group and/or a 2-hydroxyethyl group.

3. Compound as claimed in claim 1 wherein each $R^2$ denotes a hydrogen atom and/or a methyl group.

4. Compound as claimed in claim 1 wherein each $R^3$ group denotes a hydrogen atom, a methyl group and/or a 2-hydroxyethyl group.

5. Compound as claimed in claim 1 wherein each $R^2$ denotes a hydrogen atom, and each $R^3$ denotes a methyl group.

6. Compound as claimed in claim 1 wherein each $R^4$ independently denotes a mono-, di- or tri-hydroxylated $C_1$ to $C_6$ straight chain alkyl group.

7. Compound as claimed in claim 6 wherein all $R^4$ are the same and are 2,3-dihydroxypropyl moieties.

8. Compounds as claimed in claim 1 wherein each $R^5$ independently denotes a di- or tri-hydroxylated $C_1$ to $C_4$ straight chain alkyl group.

9. Compound as claimed in claim 8 wherein each $R^5$ independently denotes a di- or tri hydroxylated propyl moiety, mono- or di-hydroxyethyl moiety or hydroxymethyl.

10. Compounds as claimed in claim 1 selected from the group consisting of:

- N-(2,3-Dihydroxy-propyl)-3-(4-{3-[(2,3-dihydroxy-propyl)-methyl-carbamoyl]-5-(2-hydroxy-acetylamino)-2,4,6-triiodo-benzoyl}-piperazine-1-carbonyl)-5-(2-hydroxy-acetylamino)-2,4,6-triiodo-N-methyl-benzamide;
- 3-(2,3-Dihydroxy-propionylamino)-N-(2,3-dihydroxy-propyl)-5-(4-{3-[(2,3-dihydroxy-propyl)-methyl-carbamoyl]-3-(2,3-dihydroxy-propionylamino)-2,4,6-triiodo-benzoyl}-piperazine-1-carbonyl)-2,4,6-triiodo-N-methyl-benzamide;
- N-(2,3-Dihydroxy-propyl)-3-{4-[3-(2,3-dihydroxy-propylcarbamoyl)-5-(2-hydroxy-acetylamino)-2,4,6-triiodo-benzoyl]-piperazine-1-carbonyl}-5-(2-hydroxy-acetylamino-2,4,6-triiodo-benzamide;
- N-(2,3-Dihydroxy-propyl)-N'-(4-{3-[(2,3-dihydroxy-propyl)-methyl-carbamoyl]-5-(2-hydroxy-acetylamino)-2,4,6-triiodo-benzoylamino}-cyclohexyl)-5-(2-hydroxy-acetylamino)-2,4,6-triiodo-N-methyl-isophthalamide;
- 5-(2,3-Dihydroxy-propionylamino)-N-(2,3-dihydroxy-propyl)-N'-(4-{3-[(2,3-dihydroxy-propyl)-methyl-carbamoyl]-5-(2,3-dihydroxy-propionylamino)-2,4,6-triiodo-benzoylamino}-cyclohexyl)-2,4,6-triiodo-N-methyl-isophthalamide;
- N-(2,3-Dihydroxy-propyl)-N'-{1-[3-(2,3-dihydroxy-propylcarbamoyl)-5-(2-hydroxy-acetylamino)-2,4,6-triiodo-benzoyl]-piperidin-4-yl}-5-(2-hydroxy-acetylamino)-2,4,6-triiodo-isophthalamide;
- 3-(2,3-Dihydroxy-propionylamino)-N-(2,3-dihydroxy-propyl-5-{4-[3-(2,3-dihydroxy-propylcarbamoyl)-3-(2,3-dihydroxy-propionylamino)-2,4,6-triiodo-benzoyl]-piperazine-1-carbonyl}-2,4,6-triiodo-benzamide.

11. An X-ray diagnostic composition comprising a compound of formula (I) according to claim 1 together with pharmaceutically acceptable carriers or excipients.

12. A method of imaging comprising administration of compounds of formula (I) according to claim 1 to the human or animal body, and examining the body with a diagnostic device.

* * * * *